(12) United States Patent
Becker et al.

(10) Patent No.: US 11,931,478 B2
(45) Date of Patent: Mar. 19, 2024

(54) POST-3D PRINTING FUNCTIONALIZATION OF POLYMER SCAFFOLDS FOR ENHANCED BIOACTIVITY

(71) Applicants: Matthew Becker, Chapel Hill, NC (US); Yanyi Xu, Cuyahoga Falls, OH (US)

(72) Inventors: Matthew Becker, Chapel Hill, NC (US); Yanyi Xu, Cuyahoga Falls, OH (US)

(73) Assignee: The University of Akron, Akron, OH (US)

(*) Notice: Subject to any disclaimer, the term of this patent is extended or adjusted under 35 U.S.C. 154(b) by 457 days.

(21) Appl. No.: 16/609,772

(22) PCT Filed: May 3, 2018

(86) PCT No.: PCT/US2018/030845
§ 371 (c)(1),
(2) Date: Oct. 31, 2019

(87) PCT Pub. No.: WO2018/204611
PCT Pub. Date: Nov. 8, 2018

(65) Prior Publication Data
US 2020/0230286 A1 Jul. 23, 2020

Related U.S. Application Data

(60) Provisional application No. 62/500,777, filed on May 3, 2017.

(51) Int. Cl.
| | | |
|---|---|---|
| A61L 27/18 | (2006.01) | |
| A61L 27/38 | (2006.01) | |
| A61L 27/44 | (2006.01) | |
| A61L 27/54 | (2006.01) | |
| A61L 27/56 | (2006.01) | |
| A61L 27/58 | (2006.01) | |

(52) U.S. Cl.
CPC ........... *A61L 27/18* (2013.01); *A61L 27/3808* (2013.01); *A61L 27/3821* (2013.01); *A61L 27/3834* (2013.01); *A61L 27/44* (2013.01); *A61L 27/54* (2013.01); *A61L 27/56* (2013.01); *A61L 27/58* (2013.01); *A61L 2300/25* (2013.01); *A61L 2300/252* (2013.01); *A61L 2300/404* (2013.01); *A61L 2300/412* (2013.01); *A61L 2300/414* (2013.01); *A61L 2430/02* (2013.01)

(58) Field of Classification Search
CPC ................. A61L 2300/25; A61L 27/56; A61L 27/3821
See application file for complete search history.

(56) References Cited

U.S. PATENT DOCUMENTS

2008/0057097 A1* 3/2008 Benco ................... A61L 27/227
514/8.5

FOREIGN PATENT DOCUMENTS

| WO | 02/085246 A2 | 10/2002 |
|---|---|---|
| WO | 2012/024675 A2 | 2/2012 |
| WO | 2016/081587 A1 | 5/2016 |
| WO | 2018/144849 A1 | 8/2018 |

OTHER PUBLICATIONS

Dadsetan et al., Acta Biomaterialia, 18, 2015, 9-20.*
Pubchem: fumarate, 2 pgs.*
Dilla et al. ACS Macro Letters, 2018, 7, 1254-1260.*
Dilla et al., ACS Macro, 2018, 7, 1254-1260.*
Saito et al., Biochim Biophys Acta 1651, 2003, 60-67.*
Musammir Khan, et al. "Surface tailoring for selective endothelialization and platelet inhibition via a combination of SI-ATRP and click chemistry using Cys-Ala-Gly-peptide," Acta Biomaterialla (Elsevier, Amsterdam, NL), vol. 20, Apr. 1, 2015 (Apr. 1, 2015), pp. 69-81, XP029590351, ISSN: 1742-7061, 001: 10.1 016/J.ACTBIO.2015. 03.032.
Lin Fei, et al. "Peptide-Functionalized Oxime Hydrogels with Tunable Mechanical Properties and Gelation Behavior", Biomacromolecules, vol. 14, No. 10, Oct. 3, 2013 (Oct. 3, 2013), pp. 3749-3758, XP055815185, US ISSN: 1525-7797, 001: 10.1021/ bm401133r.
Joshua Alan Parry, et al. "Three-Dimension-Printed Porous Poly(Propylene Fumarate) Scaffolds with Delayed rhBMP-2 Release for Anterior Cruciate Ligament Graft Fixation", Tissue Engineering: Part A, vol. 23, No. 7-8, Apr. 1, 2017 (Apr. 1, 2017), pp. 359-365, XP055499699, ISSN: 1937-3341, 001: 10.1 089/ten.tea.2016.0343.
A. Melchiorri, et al. "Chemical Surface Modification of 3D Printed Poly(Propylene Fumarate) Vascular Grafts", Tissue Engineering: Part A, vol. 20, No. Supplement 1, 0-262, 2014, pp. S-20-S-21 , XP002783844.

(Continued)

*Primary Examiner* — Kyle A Purdy
(74) *Attorney, Agent, or Firm* — Renner, Kenner, Greive, Bobak, Taylor & Weber

(57) ABSTRACT

In various aspects, the present invention is directed to novel bioactive peptide loaded poly(propylene fumarate) (PPF) tissue scaffolds and related methods for their making and use. In various embodiments, these bioactive peptide loaded poly(propylene fumarate) tissue scaffolds are formed by forming a PPF structure or matrix using photochemical 3-D printing techniques and then loading that printed PPF structure or matrix with a bioactive peptides or other bioactive compounds that have, or have been functionalized to have, a thiol functional group at or near its terminus. The thiol groups on the bioactive peptides or other compound will react with exposed alkene functional groups on the PPF polymer matrix via a thiol-ene "click" reaction, thereby binding these bioactive peptides or other compounds to the tissue scaffolds. The bioactive peptide loaded PPF tissue scaffolds of the present invention are particularly useful in repairing bone defects.

12 Claims, 14 Drawing Sheets
Specification includes a Sequence Listing.

(56) References Cited

OTHER PUBLICATIONS

Haitao Cui, et al. "Hierarchical Fabrication of Engineered Vascularized Bone Biphasic Constructs via Dual 3D Bioprinting: Integrating Regional Bioactive Factors into Architectural Design," Advanced Healthcare Materials, vol. 5, No. 17, Sep. 1, 2016 (Sep. 1, 2016), pp. 2174-2181, XP055499745, DE ISSN: 2192-2640, 001: 10.1 002/ adhm.201600505.

Supporting Information for Haitao Cui, et al. "Hierarchical Fabrication of Engineered Vascularized Bone Biphasic Constructs via Dual 3D Bioprinting: Integrating Regional Bioactive Factors into Architectural Design" Adv. Healthcare Mater., DOI: 10.1002/adhm.201600505 Available online at https://onlinelibrary.wiley.com/action/downloadSupplement?doi=10.1002%2Fadhm.201600505&file=adhm201600505-sup-0001-S1.pdf.

International Search Report and Written Opinion in International Application No. PCT/US2018/030845.

* cited by examiner

POST-3D PRINTING FUNCTIONALIZATION OF POLYMER SCAFFOLDS FOR ENHANCED BIOACTIVITY

CROSS REFERENCE TO RELATED APPLICATIONS

This application claims the benefit of U.S. provisional patent application Ser. No. 62/500,777 entitled "Post-3D Printing Functionalization Polymer Scaffolds For Enhanced Bioactivity," filed May 3, 2017, and incorporated herein by reference in its entirety.

REFERENCE TO GOVERNMENT SUPPORT

This invention was made with government support under grant DMR-1105329 awarded by National Science Foundation. The government has certain rights in the invention.

FIELD OF THE INVENTION

One or more embodiments of the present invention relate to post production functionalization of polymer scaffolds with bioactive compositions. In certain embodiments, the present invention relates to functionalizing a degradable and resorbable 3D printed poly(propylene fumarate) polymer scaffold with a bioactive peptide or other compound.

SEQUENCE LISTING

The Sequence Listing file entitled "UOA1326SequenceListingST25.txt" having a size of 5,237 bytes and creation date of May 2, 2018 that was electronically filed with the patent application is incorporated herein by reference in its entirety.

NAMES OF THE PARTIES TO A JOINT RESEARCH AGREEMENT

The present application stems from work done pursuant to a Joint Research Agreement between The University of Akron of Akron, Ohio and 3D BioActives LLC of Pepper Pike, Ohio.

BACKGROUND OF THE INVENTION

Photochemically-based 3D printing is a light and heat intensive process that is inhospitable for peptides, proteins and drugs. The resins often require the use of an organic or mixed solvent to meet the viscosity requirements of the printing process. Therefore, it is very difficult to incorporate biologics using traditional manufacturing methods. Immobilization of bioactive peptides onto surfaces and 3D scaffolds following the printing process had been shown to be an effective avenue to improve cell attachment, influence proliferation, and direct differentiation in tissue engineering. Physical adsorption/encapsulation and chemical conjugation have both been applied to derivatize tissue engineering scaffolds with bioactive peptides.

What is needed in the art is an improved tissue scaffold that is degradable and resorbable and can be easily loaded with bioactive peptides or other bioactive compounds that can improve cell attachment, influence proliferation, and direct differentiation in tissue engineering.

SUMMARY OF THE INVENTION

In one or more embodiments, the present invention provide a novel bioactive peptide loaded poly(propylene fumarate) (PPF) tissue scaffolds, as well as related methods for their making and use. In various embodiments, these bioactive peptide loaded poly(propylene fumarate) tissue scaffolds are formed by 3-D printing poly(propylene fumarate) tissue scaffolds using standard photochemical 3-D printing techniques and then loading the printed PPF scaffolds with a bioactive or other bioactive compound having, or having been functionalized to have, a thiol functional group at or near its terminus. The thiol groups on the bioactive peptides or other compound will react with exposed alkene groups on the PPF polymer matrix via a thiol-ene "click" reaction, thereby binding the These bioactive peptide or other compound to the tissue scaffolds are particularly useful in repairing bone defects.

In a first aspect, the present invention is directed to a method of making a bioactive compound loaded poly(propylene fumarate) tissue scaffold comprising: preparing a 3-D printable resin comprising a poly(propylene fumarate) polymer having alkene functional groups; forming a poly(propylene fumarate) polymer structure or matrix from the 3-D printable resin using 3-D printing technology, wherein the poly(propylene fumarate) polymer structure or matrix has a surface with exposed alkene functional groups; preparing a bioactive compound having at least one thiol functional group at or near its terminus; contacting the poly(propylene fumarate) polymer structure or matrix with the bioactive compound; wherein the least one thiol functional group on the bioactive compound reacts with the alkene functional groups on the surface of the poly(propylene fumarate) polymer structure or matrix thereby tethering the bioactive peptides to the poly(propylene fumarate) polymer structure or structure or matrix to form a bioactive compound loaded tissue scaffold. In one or more embodiments, the 3-D printable resin further comprises diethyl fumarate (DEF). In one or more embodiments, the method of making a bioactive compound loaded poly(propylene fumarate) tissue scaffold of the present invention includes any one or more of the above referenced embodiments of the first aspect of the present invention wherein the 3-D printable resin further comprises at least one of photoinitiators, dyes, light attenuating agents, dispersants, emulsifiers, ceramics, BIO-GLASS™, hydroxyapatite, β-tricalcium phosphate, and solvents. In one or more embodiments, the method of making a bioactive compound loaded poly(propylene fumarate) tissue scaffold of the present invention includes any one or more of the above referenced embodiments of the first aspect of the present invention wherein the structure or matrix is porous.

In one or more embodiments, the method of making a bioactive compound loaded poly(propylene fumarate) tissue scaffold of the present invention includes any one or more of the above referenced embodiments of the first aspect of the present invention wherein the poly(propylene fumarate) polymer has a number average molecular weight ($M_n$) as measured by size exclusion chromatography or mass spectroscopy of from about 500 g/mole to about 10,000 g/mole. preferably from 1000 g/mole to 5000 g/mole, and more preferably from 1000 g/mole to 3000 g/mole. In one or more embodiments, the method of making a bioactive compound loaded poly(propylene fumarate) tissue scaffold of the present invention includes any one or more of the above referenced embodiments of the first aspect of the present invention wherein the poly(propylene fumarate) polymer has a polydispersity index ($Ð_m$) as measured by size exclusion chromatography of from about 1.0 to about 2.0, preferably from about 1.05 to about 1.6, and more preferably from about 1.05 to about 1.2.

In one or more embodiments, the method of making a bioactive compound loaded poly(propylene fumarate) tissue scaffold of the present invention includes any one or more of the above referenced embodiments of the first aspect of the present invention wherein the bioactive compound is a bioactive peptide. In one or more embodiments, the method of making a bioactive compound loaded poly(propylene fumarate) tissue scaffold of the present invention includes any one or more of the above referenced embodiments of the first aspect of the present invention wherein the bioactive peptide is an angiogenetic peptide, osteogenic peptide or antimicrobial peptide. In one or more embodiments, the method of making a bioactive compound loaded poly(propylene fumarate) tissue scaffold of the present invention includes any one or more of the above referenced embodiments of the first aspect of the present invention wherein the bioactive compound is a bioactive peptide selected from the group consisting of basic fibroblast growth factor (bFGF) (SEQ. ID NO. 1), Bone Morphogenetic Protein 2 (BMP-2) (SEQ. ID NO. 2), Osteogenic Growth Peptide (OGP), 10-14 (YGFGG) (SEQ. ID NO. 3), BMP-2 73-92 (KIPKASSVP-TELSAISTLYL) (SEQ. ID NO. 4), BMP-7 89-117 (TVPKPSSAPTQLNAISTLYF) (SEQ. ID NO. 5), BMP-9 68-87 (KVGKASSVPTKLSPISILYK) (SEQ. ID NO. 6), and combinations thereof. In one or more embodiments, the method of making a bioactive compound loaded poly(propylene fumarate) tissue scaffold of the present invention includes any one or more of the above referenced embodiments of the first aspect of the present invention wherein the bioactive peptide has a terminal cysteine residue.

In one or more embodiments, the method of making a bioactive compound loaded poly(propylene fumarate) tissue scaffold of the present invention includes any one or more of the above referenced embodiments of the first aspect of the present invention further comprising seeding the tissue scaffold with cells; and growing the cells on the tissue scaffold. In one or more embodiments, the method of making a bioactive compound loaded poly(propylene fumarate) tissue scaffold of the present invention includes any one or more of the above referenced embodiments of the first aspect of the present invention wherein the cells are selected from the group consisting of endothelial cells, osteocytes, mesenchymal stem cells, osteoblasts, and combinations thereof.

In a second aspect, the present invention is directed to a method of post-production functionalization of a 3-D printed poly(propylene fumarate) polymer structure with bioactive peptides comprising: preparing a 3-D printable resin comprising a poly(propylene fumarate) polymer having alkene functional groups; 3-D printing a poly(propylene fumarate) polymer structure from a 3-D printable resin containing a poly(propylene fumarate) polymer having one or more alkene functional groups, wherein the poly(propylene fumarate) polymer structure or matrix has a surface with exposed alkene functional groups; preparing a bioactive peptide having at least one thiol functional group at or near the end terminus; contacting the 3-D poly(propylene fumarate) polymer matrix or structure with the bioactive peptides; wherein the least one thiol functional group on the bioactive peptides reacts with the alkene functional groups on the surface of the poly(propylene fumarate) polymer matrix/structure thereby tethering the bioactive peptides to the poly(propylene fumarate) polymer matrix/structure or matrix to form a bioactive peptide loaded tissue scaffold. In one or more of these embodiments, the step of preparing further comprises dissolving the bioactive peptide in a buffered aqueous solvent and adding a photoinitiator to form a peptide solution and the step of contacting further comprises contacting the 3-D poly(propylene fumarate) polymer structure with the peptide solution and irradiating it with ultraviolet light. In one or more embodiments, the PPF structure or matrix is porous.

In a third aspect, the present invention is directed to a bioactive compound loaded poly(propylene fumarate) tissue scaffold formed according to the method described above comprising: a poly(propylene fumarate) polymer structure or matrix; and a plurality of bioactive compounds, wherein the plurality of bioactive compounds are tethered to the poly(propylene fumarate) polymer structure or matrix by thiol-ene bonds. In one or more of these embodiments, bioactive compounds are bioactive peptides. In one or more embodiments, the bioactive compound loaded poly(propylene fumarate) tissue scaffold of the present invention includes any one or more of the above referenced embodiments of the third aspect of the present invention wherein the structure or matrix further comprises one or more of photoinitiators, dyes, light attenuating agents, dispersants, emulsifiers, ceramics, BIOGLASS™, hydroxyapatite, 3-tricalcium phosphate, and solvents. In one or more embodiments, the bioactive compound loaded poly(propylene fumarate) tissue scaffold of the present invention includes any one or more of the above referenced embodiments of the third aspect of the present invention wherein the poly(propylene fumarate) polymer structure or matrix is formed by 3-D printing.

In one or more embodiments, the bioactive compound loaded poly(propylene fumarate) tissue scaffold of the present invention includes any one or more of the above referenced embodiments of the third aspect of the present invention wherein the bioactive peptides comprise at least one of angiogenic peptides, osteogenic peptides, and antimicrobial peptides. In one or more embodiments, the bioactive compound loaded poly(propylene fumarate) tissue scaffold of the present invention includes any one or more of the above referenced embodiments of the third aspect of the present invention wherein the bioactive peptides are selected from the group consisting of basic fibroblast growth factor (bFGF) (CYKRSRYT (SEQ. ID NO. 1)), Bone Morphogenetic Protein 2 (BMP-2) (CKIPKASSVPTELSAISTLYL (SEQ. ID NO. 2)), Osteogenic Growth Peptide (OGP), 10-14 (YGFGG) (SEQ. ID NO. 3), BMP-2 73-92 (KIPKASSVPTELSAISTLYL) (SEQ. ID NO. 4), BMP-7 89-117 (TVPKPSSAPTQLNAISTLYF) (SEQ. ID NO. 5), BMP-9 68-87 (KVGKASSVPTKLSPISILYK) (SEQ. ID NO. 6), and combinations thereof.

In one or more embodiments, the bioactive compound loaded poly(propylene fumarate) tissue scaffold of the present invention includes any one or more of the above referenced embodiments of the third aspect of the present invention further comprising a plurality of cells adhered to the poly(propylene fumarate) tissue scaffold. In one or more embodiments, the bioactive compound loaded poly(propylene fumarate) tissue scaffold of the present invention includes any one or more of the above referenced embodiments of the third aspect of the present invention wherein the cells are selected from the group consisting of endothelial cells, osteocytes, mesenchymal stem cells, osteoblasts, and combinations thereof.

In a fourth aspect, the present invention is directed to a method of repairing a bone defect using the bioactive compound loaded poly(propylene fumarate) tissue scaffold described above comprising: identifying a bone defect in a patient that is in need of repair; preparing a bioactive compound loaded poly(propylene fumarate) tissue scaffold described above that is sized to fit within the bone defect; and surgically inserting the peptide loaded poly(propylene fumarate) tissue scaffold into the bone defect; allowing the patient's bone to regrow in the bone defect using the bioactive compound loaded poly(propylene fumarate) tissue scaffold.

In one or more of these embodiments, the step of preparing a bioactive peptide loaded poly(propylene fumarate) tissue scaffold comprises: preparing a 3-D printable resin comprising a poly(propylene fumarate) polymer having alkene functional groups; 3-D printing a poly(propylene fumarate) polymer structure sized to fit within the bone defect from a 3-D printable resin containing a poly(propylene fumarate) polymer having one or more alkene functional groups, wherein the poly(propylene fumarate) polymer structure or matrix has a surface with exposed alkene functional groups; preparing a plurality of bioactive peptides having at least one thiol functional group at or near the end terminus; contacting the 3-D poly(propylene fumarate) polymer structure with the bioactive peptides; wherein the least one thiol functional group on the bioactive peptides reacts with the alkene functional groups on the surface of the poly(propylene fumarate) polymer structure thereby tethering the bioactive peptides to the poly(propylene fumarate) polymer structure or matrix to form a bioactive peptide loaded tissue scaffold. In one or more of these embodiments, the bioactive peptide comprises at least one of an angiogenic peptide, an osteogenic peptide, and an antimicrobial peptide.

BRIEF DESCRIPTION OF THE DRAWINGS

For a more complete understanding of the features and advantages of the present invention, reference is now made to the detailed description of the invention along with the accompanying figures in which:

FIG. 4C is a control (Mean Intensity: 1197.13±11.11). PPF scaffold click reaction (0.1 μM dye+0.05 μM initiator).

FIGS. 6A and 6B are top views and FIG. 6C is a cross sectional view.

FIG. 8A is an image of cells spreading on a PPF polymer film and FIG. 8B is an image of cells spreading on a PPF polymer film functionalized with bFGF according to one or more embodiments of the present invention. Cell type: hMSCs P5. Cell original seeding density: 198 cells/mm$^2$ (same for scaffold). Time: 3 days after cell seeding. Thin films thickness: 100-150 μm. Plates were coated with Poly-HEMA first to ensure cell adhesion on thin film.

DETAILED DESCRIPTION OF THE ILLUSTRATIVE EMBODIMENTS

Figure 1:
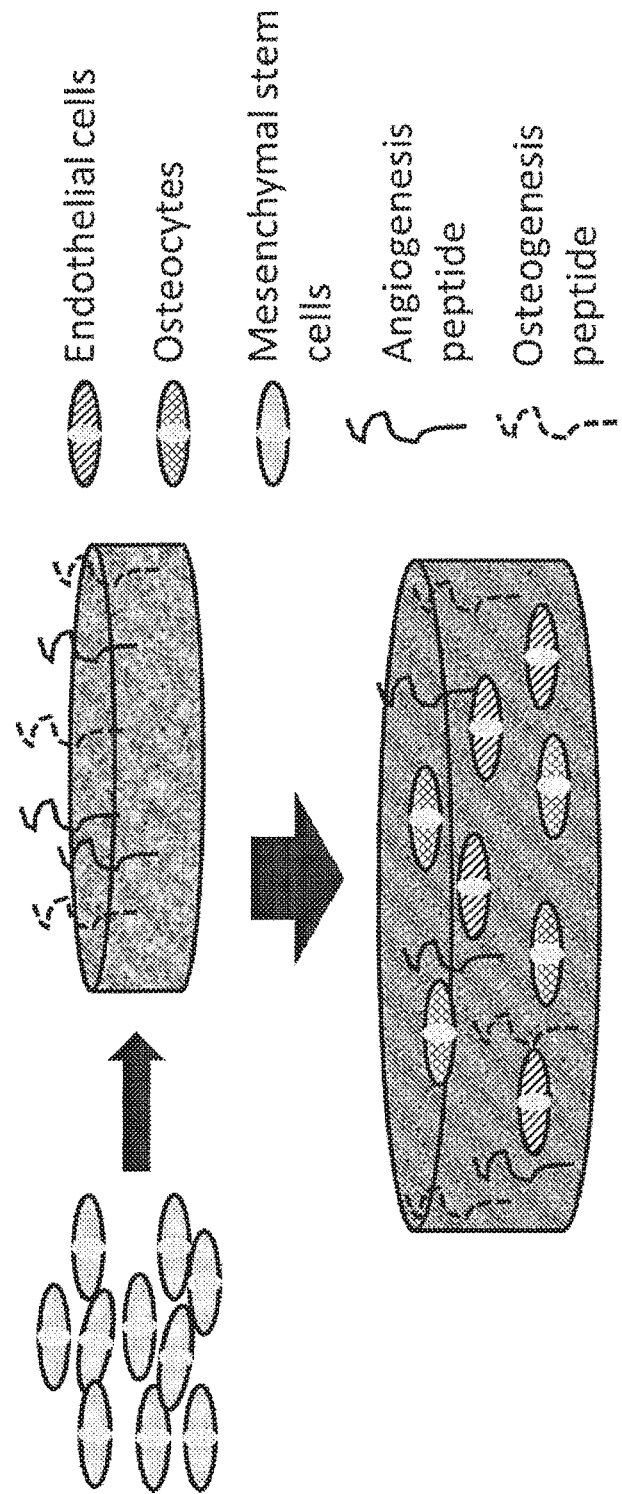
FIG. 1 is schematic diagram showing seeding of a bioactive peptide loaded poly(propylene fumarate) tissue scaffold according to one or more embodiments of the present invention with mesenchymal stem cells and the subsequent differentiation of these cells into endothelial cells and osteocytes.

In various aspects, the present invention is directed to novel bioactive peptide loaded poly(propylene fumarate) (PPF) tissue scaffolds and related methods for their making and use. In various embodiments, these bioactive peptide loaded poly(propylene fumarate) tissue scaffolds are formed by forming a poly(propylene fumarate) structure or matrix using photochemical 3-D printing techniques and then loading that printed PPF structure or matrix with a bioactive peptides or other bioactive compounds that have, or have been functionalized to have, a thiol functional group at or near its terminus. The thiol groups on the bioactive peptides or other compound will react with exposed alkene functional groups on the PPF polymer matrix via a thiol-ene "click" reaction, thereby binding these bioactive peptides or other compounds to the tissue scaffolds. The bioactive peptide loaded poly(propylene fumarate) (PPF) tissue scaffolds of the present invention are particularly useful in repairing bone defects.

In a first aspect, the present invention is directed to a method of making a bioactive peptide loaded poly(propylene fumarate) tissue scaffold. In general outline, the method involves the following steps: (1) preparing a 3-D printable resin comprising a poly(propylene fumarate) polymer having alkene functional groups; (2) forming a poly(propylene fumarate) polymer structure or matrix from 3-D printable resin having a surface with exposed alkene functional groups using 3-D printing technology; (3) selecting and/or preparing a bioactive peptide or other bioactive compound having at least one thiol functional group at or near its terminus; and (4) contacting the poly(propylene fumarate) polymer matrix with the bioactive peptide such that the thiol functional groups on said bioactive peptides will reacts with the alkene functional groups on the surface of said poly(propylene fumarate) polymer matrix to tether the bioactive peptides to the poly(propylene fumarate) polymer matrix to form the bioactive peptide loaded tissue scaffold of the present invention.

As set forth above, the bioactive peptide loaded tissue scaffolds of the present invention are formed from poly(propylene fumarate) (PPF) polymers. These polymers have been found to be very well suited to this application. They are known to be degradable, well defined, and have tunable mechanical properties that make them particularly well suited to these applications. PPF polymers are particularly well suited for use in resins for 3D printing, particularly with standard photochemical and/or stereolithographic 3D printers.

In various embodiments, poly(propylene fumarate) (PPF) used to form the bioactive peptide loaded PPF tissue scaffolds of the present invention is not particularly limited. However, the PPF polymers used to form the bioactive peptide loaded PPF tissue scaffolds of the present invention are preferably prepared using ring-opening methods such as the one shown in Scheme 1 below.

Scheme 1

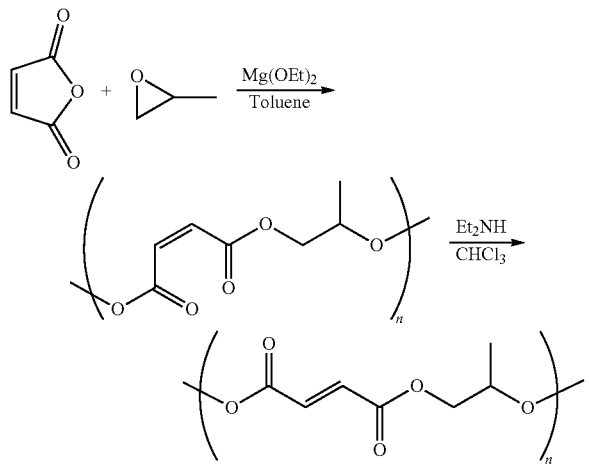

where n the number of propylene maleate or propylene fumarate units. In one or more embodiments, n is an integer from about 3 to about 30. In some embodiments, n is an integer from about 5 to about 30, in other embodiments, from about 10 to 30, in other embodiments, from about 15 to 30, in other embodiments, from about 3 to 25, in other embodiments, from about 3 to 20, in other embodiments, from about 3 to 15, and in other embodiments, from about 3 to 10. In some embodiments, the poly(propylene fumarate) polymer used in the 3-D printable resin used in the method of making a bioactive peptide loaded poly(propylene fumarate) tissue scaffold of the present invention may be synthesized as shown in international (PCT) patent application number PCT/US2015/061314, published as WO 2016/018587, the disclosure of which is incorporated herein by reference in its entirety. PPF polymers are degradable, well defined, and have tunable mechanical properties that make them particularly well suited to these applications.

In some embodiments, the poly(propylene fumarate) polymer has a number average molecular weight as measured by size exclusion chromatography or mass spectroscopy of from about 500 g/mole to about 10,000 g/mole, preferably from 1000 g/mole to 5000 g/mole, and more preferably from 1000 g/mole to 3000 g/mole. In some embodiments, the PPF polymer may have a $M_n$ of from about 500 g/mole to about 8000 g/mole, in other embodiments, from about 500 g/mole to about 6000 g/mole, in other embodiments, from about 500 g/mole to about 4000 g/mole, in other embodiments, from about 500 g/mole to about 2000 g/mole, in other embodiments, from about 800 g/mole to about 10000 g/mole, in other embodiments, from about 1500 g/mole to about 10000 g/mole, in other embodiments, from about 3000 Da to about 10000 g/mole and in other embodiments, from about 5000 g/mole to about 10000 g/mole.

In some embodiments, the poly(propylene fumarate) polymer has a polydispersity index or molecular mass distribution ($Đ_M$) as measured by size exclusion chromatography of from about 1.0 to about 2.0, preferably from 1.05 to 1.6, and more preferably from 1.05 to 1.2. The terms polydispersity index and molecular mass distribution ($Đ_M$) are used interchangeably to refer to the ratio of weight average molecular mass ($M_w$) to the mass average molecular mass ($M_n$) as measured by size exclusion chromatography. In some embodiments, the PPF polymer will have a $Đ_m$ of from about 1.0 to about 1.8, in some embodiments, from about 1.0 to about 1.6, in some embodiments, from about 1.0 to about 1.4, in some embodiments, from about 1.0 to about 1.2, in some embodiments, from about 1.1 to about 2.0, in some embodiments, from about 1.3 to about 2.0, in some embodiments, from about 1.5 to about 2.0, and in some embodiments, from about 1.7 to about 2.0.

In one or more embodiments, the PPF polymer is mixed with diethyl fumarate (DEF) (Sigma-Aldrich, St. Louis, MO) to form an initial PPF resin and for storage. In one or more embodiments, the DEF serves both as a solvent for the PPF and as a crosslinking agent when the polymer is later printed and cured. In some embodiments, the poly(propylene fumarate):diethyl fumarate (PPF:DEF) ratio in the initial PPF resin is about 3:1. To begin the preparation of the 3-D printable resin for making the peptide loaded PPF tissue scaffolds of the present invention the initial PPF resin is diluted with DEF as a solvent to reach a viscosity necessary for use with the particular 3D printer to be used. In some embodiments, the initial PPF resin is diluted to a 1:1 PPF:DEF ratio using additional DEF be cured as thin films or 3D printed. resin was diluted to 1:1 using additional DEF.

In addition to the PPF polymer and DEF solvent/crosslinker described above, the 3-D printable resin is in various embodiments of the present invention may further comprise one or more other additives such as photoinitiators, dyes, light attenuating agents, dispersants, emulsifiers, ceramics, bioglass, hydroxyapatite, β-tricalcium phosphate, crosslinkers and/or solvents. The photoinitiators that may be used in the 3-D printable resin of embodiments of the present invention are not particularly limited and may be any photoinitiator capable of producing a radical at a suitable wavelength (approximately 254-450 nm). As will be appreciated by those of skill in the art, the choice of photoinitiator is often dictated by the requirements of the 3D printer being used, but suitable photoinitiators may include, without limitation, IRGACURE™ 819/BAPO (BASF, Florham Park, NJ) or IRGACURE™ 784 (BASF, Florham Park, NJ), The dyes that may be used in the 3-D printable resin of embodiments of the present invention are not particularly limited and may any dye conventionally used in 3D printing, provided that it does not quench the radicals necessary for crosslinking. The light attenuating agents that may be used in the 3-D printable resin of embodiments of the present invention are not particularly limited and may include, without limitation, Oxybenzone (2-Hydroxy-4-methoxybenzophenone) (Sigma-Aldrich). The emulsifiers that may be used in the 3-D printable resin of embodiments of the present invention are not particularly limited and may include, without limitation, sucrose, threhalose, or any sugar molecule.

In various embodiments, the 3-D printable resin of embodiments of the present invention may include one or more other additives to support and/or promote tissue growth. The additives are not particularly limited provided that they do not quench the radicals needed for crosslinking of the 3-D printable resin. In various embodiments, the 3-D printable resin may contain additives such as, ceramics, BIOGLASS™, hydroxyapatite, β-tricalcium phosphate, and combinations thereof.

In various embodiments, the various resin components described above (e.g. photoinitiators, dyes, light attenuating agents, dispersants, emulsifiers, ceramics, bioglass, hydroxyapatite, β-tricalcium phosphate, crosslinkers and/or solvents) may be added to the 3-D printable resin at any time prior to crosslinking of the PPF polymer, as described below.

As set forth above, the PPF polymer structure/matrix may be formed from the 3-D printable resin described above using any available 3-D printing technology, but is preferably formed on a 3-D printer using photochemical 3-D printing technology. The terms "structure" and "matrix" are used interchangeably to refer to the solid and shaped PPF polymer used to form the bioactive peptide loaded poly(propylene fumarate) tissue scaffolds of the present invention. Since the method of PPF structure formation does not directly affect the thiol-ene "click" reaction between the PPF polymer and the thiol group on the peptide, in various embodiments the PPF structure used to form the scaffolds of the present invention may be formed using other methods such as extrusion, bioprinting, coating, casting, or injection molding. 3-D printing is preferred, however, because it more easily provides for customer design of complex geometries, has a high resolution, and can provide tunable mechanical properties and degradation properties, when compared to other methods.

In one or more embodiment, the PPF polymer matrix may be formed using a standard photochemical and/or stereolithographic 3D printer. Suitable 3-D printers may include, without limitation, Carbon3D printers (CARBON3D™, Redwood City, CA), PERFACTORY™ P3 3D printer (EnvisionTEC, Dearborn, MI), photocentric stereolithographic or photochemical 3D printers.

In various embodiments, the PPF polymer matrix may be formed by first generating a set of instructions for 3-D printing a desired structure and sending those instructions to a suitable 3-D printer. In some of these embodiments, the set of instructions may comprise a computer assisted design (CAD) file generated using suitable computer software that are readable by the 3D printer to be used. In one or more embodiments, the CAD or other computer file containing instructions for printing the poly(propylene fumarate) polymer matrix may be generated as set forth in U.S. Pat. Nos. 6,849,223, 7,702,380, 7,747,305, 8,781,557, 9,208,558, 9,275,191, 9,292,920, 9,330,206, 9,626,756, 9,672,302, 9,672,617, and 9,688,023, the disclosures of which are incorporated herein by reference in their entirety.

In one or more embodiments, the PPF polymer structure/matrix may have any size or shape that can be formed using 3-D printing. In some embodiments, the PPF polymer structure/matrix may be formed into such things as films, pins, plates, screws, medical devices, scaffolds, and portions thereof or coatings thereon. In various embodiments, the PPF polymer matrix is configured to fit within a bone defect. In some embodiments, the PPF polymer matrix formed is porous. As used herein, the term "porous" as applied to the PPF polymer structure/matrix or the bioactive peptide loaded PPF tissue scaffold of the present invention refers generally to a structure having one or more pores, voids, or other openings in the PPF structure/matrix, and more particularly to those pores, voids, or other openings in the PPF structure/matrix that are open to the outside of the structure and increase the overall surface area to which the bioactive compounds can be (or are) attached. As will be apparent to those of skill in the art, a more porous structure provides more surface area for bioactive peptides and/or other bioactive compounds to attach to the matrix. While this can be advantageous, the poly(propylene fumarate) polymer matrix should not be so porous as to lose the structural integrity necessary for the particular application for which it is being used.

In some of these embodiments, the PPF polymer matrix may have a porosity of from about 1% to about 95% preferably from about 10% to about 90% and more preferably from about 50% to about 85%, as measured by x-ray microcomputed tomography. On some embodiments, the PPF polymer matrix may have a porosity of from about 5% to about 95%, in other embodiments, from about 10% to about 95%, in other embodiments, from about 20% to about 95%, in other embodiments, from about 30% to about 95%, in other embodiments, from about 50% to about 95%, in other embodiments, from about 60% to about 95%, in other embodiments, from about 75% to about 95%, in other embodiments, from about 1% to about 85%, in other embodiments, from about 1% to about 75%, in other embodiments, from about 1% to about 65%, in other embodiments, from about 1% to about 55%, and in other embodiments, from about 1% to about 45%.

In some embodiments, the poly(propylene fumarate) polymer matrix is formed as a porous cylindrical structure with Schoen Gyroid triply periodic minimal surface geometry having a strut diameter of from 10 μm to 1000 μm, preferably from about 50 μm to about 500 μm, and more preferably from about 100 μm to about 200 μm; a pore diameter of from 200 μm to 2000 μm, preferably from about 300 μm to about 1000 μm, and more preferably from about 400 μm to about 800 μm. In some embodiments, In some embodiments, the poly(propylene fumarate) polymer matrix may Schoen Gyroid triply periodic minimal surface geometry with a diameter of 5 mm, a thickness of 150 μm, 83% porosity, and a pore diameter of 400 μm.

In one or more embodiments, the desired structure is then 3-D printed using the 3-D printable resin described above, based upon the instructions provided to the particular 3D printer being used. In one or more embodiments, the desired structure for the PPF polymer matrix may be printed from the PPF resin described above using an PERFACTORY™ P3 3D printer (EnvisionTEC, Dearborn, MI).

In one or more embodiments, the newly printed 3D PPF matrix is then cured by exposing it to ultraviolet light for a period of from about 1 minute to about 10 hours, preferably from about 1 minute to about 1 hour, and most preferably from about 1 minute to about 5 minutes to photochemically crosslink the newly printed 3D PPF structure. As will be appreciated, the newly printed 3D PPF matrix should be cured long enough to permit sufficient crosslinking to provide the necessary rigidity and strength for the desired use but not so long that the UV irradiation damages the polymer. In one or more embodiments, the newly printed 3D PPF matrix is cured from about 5 seconds to about 500 seconds. In some embodiments, the newly printed 3D PPF matrix is cured from about 5 seconds to about 400 seconds, in other embodiments, from about 5 seconds to about 400 seconds, in other embodiments, from about 5 seconds to about 300 seconds, in other embodiments, from about 5 seconds to about 200 seconds, in other embodiments, from about 30 seconds to about 500 seconds, in other embodiments, from about 60 seconds to about 500 seconds, in other embodiments, from about 120 seconds to about 500 seconds, and in other embodiments, from about 200 seconds to about 500 seconds. In one or more embodiments, 3D structures for use in the scaffolds of the present invention may be printed using a PERFACTORY™ P3 3D printer (EnvisionTEC, Dearborn, MI) which was calibrated to produce a UV mask with a nominal irradiance at 350 mWdm$^{-2}$. In one or more embodiments, the newly printed 3D PPF structures may be cured by exposing it to ultraviolet light using a PROCURE™ UV box (3D Systems, Rock Hill, SC).

Once the newly printed 3D structure is fully cured, it is then rinsed to remove any uncured resin. In some embodiments the step of rinsing away the uncured resin comprises rinsing said structure with a buffered water miscible solvent solution. Suitable water miscible solvents may include, without limitation, acetone, methanol, or ethanol, or a combination thereof, but is preferably acetone. The water miscible solvents may be buffered with any suitable buffer solution that buffers to a biologically appropriate pH, but are preferably buffered with Phosphate Buffered Saline (PBS).

As set forth above, in various embodiments, a suitable bioactive peptide or other bioactive compound is then added to the 3D printed PPF tissue structure described above to form the bioactive peptide loaded PPF tissue scaffold of the present invention. While the methods for attaching bioactive peptides or other bioactive compounds are discussed in the context of adding them to the 3D printed PPF tissue scaffolds discussed above, the invention is not to be so limited as the methods described below are equally applicable to other structures made in whole or in part, from crosslinking the 3-D printable resin described above, such as films, pins, plates, screws, medical devices, and scaffolds (including portions thereof or coatings thereon), and includes structures made by means other than 3D printing such as, extrusion, bioprinting, coating, casting, or injection molding.

As will be apparent to those of ordinary skill in the art, each propylene fumarate unit in the PPF polymer forming the 3D printed structure described above contains a reactive trans double bond in the fumaric unit of the PPF polymer that is capable of bonding with a thiol group via a. thiol-ene "click" reaction, This thiol-ene "click" reaction may be photoinitiated but it does not need to be for the reaction to take place. As will be appreciated, use of a photoinitiator will increase rate of the thiol-ene "click" reaction and with it, the speed at which the bioactive peptide or other bioactive compound may be added to the 3D printed PPF tissue scaffold.

As will be apparent, for the bioactive peptide or other bioactive compound to be attached to the 3D printed PPF tissue scaffold or other structure described above, it must have at least one thiol functional group that is capable of reacting with the alkene functional groups on the surface of the PPF polymer matrix via the thio-ene "click" reaction described above. In one or more embodiments, the thiol functional group will be located a terminus, but it need not be provided that it is in a location where it is free to react with the alkene functional groups on the surface of the 3D printed PPF tissue scaffold. In various embodiments, the bioactive peptide or other bioactive compound to be attached is a bioactive peptide having a naturally occurring terminal cysteine residue.

In some other embodiments, the bioactive peptide or other bioactive compound to be attached lacks a naturally occurring terminal cysteine or other available thiol functional group. In these embodiments, the bioactive peptide to be attached may be functionalized to include the thiol group by any means known in the art for doing so. However, care must be taken to make sure that the reaction used to attach the available thiol functional group does not unduly denature the peptide or render it unsuitable for its intended use.

In various embodiments, suitable bioactive peptides may be collected or synthesized by any conventional means. In one or more embodiments, suitable bioactive peptides may be formed using standard peptide synthesis methods including, but not limited to, Fmoc solid-state peptide synthesis. In some of these embodiments, suitable bioactive peptides may be prepared by Fmoc solid-state peptide synthesis using a Liberty 1 peptide synthesizer (CEM Corporation, Matthews, NC) by loading a Wang resin containing the appropriate C-terminal amino acid of the sequence in the synthesizer and adding additional amino acids by subjected it to various deprotection and coupling steps under microwave irradiation as is known in the art to yield the target peptide.

On one or more embodiments, the bioactive peptide used to make the bioactive peptide loaded PPF tissue scaffolds of the present invention is an angiogentic peptide, osteogenic peptide or antimicrobial peptide. In various embodiments, suitable bioactive peptides may include, without limitation, basic fibroblast growth factor (bFGF) (CYKRSRYT (SEQ. ID NO. 1)), Bone Morphogenetic Protein 2 (BMP-2) (CK-IPKASSVPTELSAISTLYL (SEQ. ID NO. 2)), Osteogenic Growth Peptide (OGP), 10-14 (YGFGG (SEQ. ID NO. 3)), BMP-2 73-92 (KIPKASSVPTELSAISTLYL (SEQ. ID NO. 4)), BMP-7 89-117 (TVPKPSSAPTQLNAISTLYF (SEQ. ID NO. 5)), BMP-9 68-87 (KVGKASSVPTKLSPISILYK (SEQ. ID NO. 6)), or a combination thereof. bFGF (basic fibroblast growth factor) (CYKRSRYT) (SEQ. ID NO. 1) is known to be involved in angiogenesis and induces MSCs differentiation into endothelial cells. BMP-2 (bone morphogenetic protein 2) (CKIPKASSVPTELSAISTLYL (SEQ. ID NO. 2)) has been shown to induce the mitogenesis of mesenchymal stem cells (MSCs) and MSCs differentiation into osteoblasts.

While the PPF tissue scaffolds of the present invention described herein as "peptide loaded" it should be appreciated that bioactive materials other than peptides may be added to the PPF tissue scaffolds of the present invention.

Other bioactive compounds like proteins, growth factors, drugs, prodrugs, that have, or are functionalized to have, at least one available thiol functional group may also be used. The bioactive compounds that may be used are only limited by the availability of the thiol group for bonding.

In some embodiments, a terminal cysteine residue may be added to a desired bioactive peptide during Fmoc solid-state peptide synthesis as described above. In one or more embodiments, the bioactive peptide may have the formula:

ing them in a buffered aqueous solution containing a water miscible solvent to form a peptide solution, which is then brought in contact with the 3D printed PPF matrix to allow the thiol-ene reaction to occur. Suitable water miscible solvents may include, without limitation, dimethylformamide (DMF) mixtures. In various embodiments, these water miscible solvents may be buffered with any suitable buffer solution that buffers to a biologically appropriate pH, but are preferably buffered with Phosphate Buffered Saline (PBS).

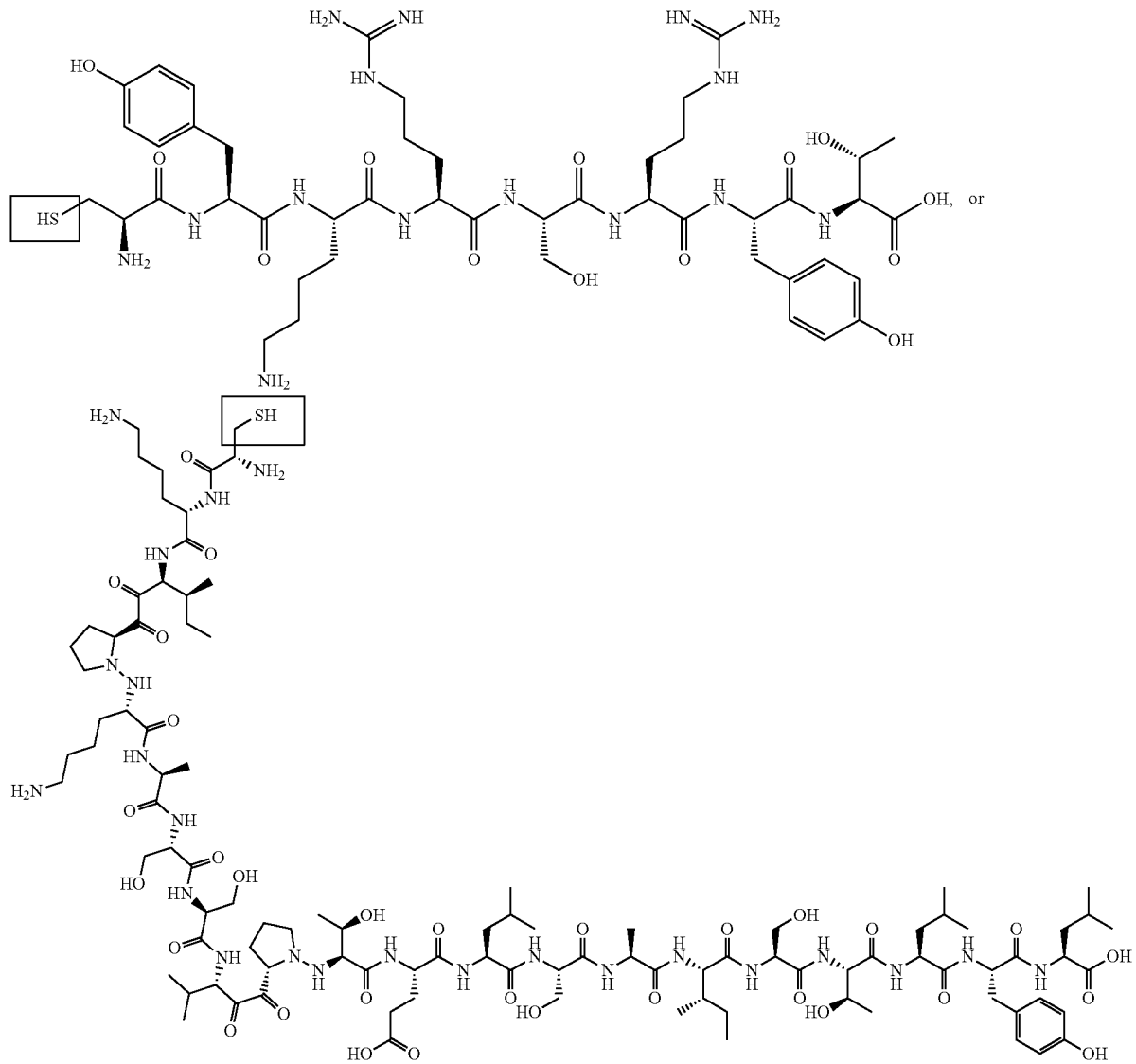

Once the bioactive peptide or bioactive compound to be attached has been prepared, it is tethered to the 3D printed PPF matrix by means of a thiol-ene "click reaction" between the thiol groups on the bioactive peptides or bioactive compounds to be attached and the alkene groups on the surface of the 3D printed PPF matrix, as set forth above. In various embodiments, the thiol-ene "click reaction" may or may not be photoinitiated and can take place at ambient temperature under conditions that do not damage the peptides or other bioactive compounds being attached. In one or more embodiments, the peptides or other bioactive compounds are added to 3D printed PPF matrix by first dissolv- In some embodiments, the peptides or other bioactive compounds to be attached are dissolved in a 100:1 v/v mixture of phosphate-buffered saline (PBS) and dimethylformamide (DMF).

As will be appreciated by those of ordinary skill in the art, the peptide solution must be brought into contact with, and kept in contact with, the PPF polymer matrix long enough to allow the thiol-ene "click" reaction that bonds the peptide or other bioactive material to the exposed surfaces of the 3D printed PPF matrix to occur. The method used to bring the peptide solution in contact with the PPF polymer matrix is not particularly limited provided that the peptide solution can be kept in contact with the PPF polymer matrix long enough to allow the thiol-ene reaction that bonds the peptide or other bioactive material to the exposed surfaces of the 3D printed PPF matrix to occur. In various embodiments, the peptide solution may be brought into contact with the PPF polymer matrix by emersion of the 3D printed PPF matrix in the peptide solution, spray coating the 3D printed PPF matrix with the peptide solution, or combinations thereof.

In some of these embodiments, the peptide solution is kept in contact with, the PPF polymer matrix long for from about 30 seconds to 2 hours in order to allow time for the thiol-ene "click" reaction that bonds the peptide or other bioactive material to the exposed surfaces of the 3D printed PPF matrix to occur. In some embodiments, the peptide solution is kept in contact with the PPF polymer matrix for from about 1 minute to about 2 hours, in other embodiments, from about 30 minutes to about 2 hours, in other embodiments, from about 45 minutes to about 2 hours, in other embodiments, from about 1 hour to about 2 hours, in other embodiments, from about 90 minutes to about 2 hours, in other embodiments, from about 30 seconds to 90 minutes, in other embodiments, from about 30 seconds to 60 minutes, in other embodiments, from about 30 seconds to 45 Minutes, and in other embodiments, from about 30 seconds to 30 minutes in order to allow the thiol-ene "click" reaction that bonds the peptide or other bioactive material to the exposed surfaces of the 3D printed PPF matrix to occur.

In some of these embodiments, the peptide solution will also contain a suitable photoinitiator. The method used to bring the peptide solution in contact with the 3D printed PPF matrix is not particularly limited provided that the peptide solution is kept in contact with the peptide solution long enough to allow the thiol-ene reaction that bonds the peptide or other bioactive material to the exposed surfaces of the 3D printed PPF matrix to occur, and may include, without limitation, emersion of the 3D printed PPF matrix in the peptide solution, spray coating the 3D printed PPF matrix with the peptide solution, or combinations thereof.

In embodiments where a photoinitiator has been added to the peptide solution, the 3D printed PPF matrix is then exposed to ultraviolet light while in contact with the peptide solution to promote the thiol-ene reaction between the thiol functional groups on the peptides or other bioactive compounds to be attached and the alkene functional groups on the PPF polymers available for bonding on the surface of the 3D printed PPF matrix. As will also be apparent, the peptide solution containing the photoinitiator must be in contact with the 3D printed PPF matrix when it is irradiated with UV light for the photochemically assisted thiol-ene "click" reactions between the thiol functional groups on the peptides or other bioactive compounds being attached and the alkene functional groups on the PPF polymers available for bonding on the surface of the 3D printed PPF matrix to occur.

The photoinitiators that may be used to assist in the attachment of the peptides and/or other bioactive compounds to the 3D printed PPF matrix in these embodiments of the present invention are not particularly limited and may be any photoinitiator capable of producing a radical at a suitable wavelength (approximately 254-450 nm) and is otherwise compatible with the both the 3D printed PPF matrix (and its component parts/additives and the peptides or other bioactive compounds to be attached at the concentrations to be used. Suitable photoinitiators may include, without limitation, Irgacure 2959 (BASF, Florham Park, NJ). As should also be apparent, the wavelengths of UV light used will be determined by the requirements of the particular photoinitiator chosen, but will ordinarily be a wavelength of from about 254 nm to about 450 nm.

In these embodiments, the 3D printed PPF matrix is exposed to ultraviolet light at an appropriate wavelength for the photoinitiator being used for from about 5 to about 500 seconds to maximize attachment of the peptides or other bioactive compounds to be attached to the surface of the 3D printed PPF matrix. However, in these embodiments, care must be taken to ensure that the UV irradiation does not damage the peptides or other bioactive compound being attached. As will be appreciated, the sensitivity to damage will vary to some degree with the nature of the particular peptide or other bioactive compound being attached. But, in general, the longer the UV irradiation, the greater the chances of damaging the peptides or other bioactive compounds being attached, and it has been found that, in general, the peptides or other bioactive compounds being attached should not be irradiated for more than about 500 seconds.

In some of these embodiments, the 3D printed PPF matrix is exposed to ultraviolet light at an appropriate wavelength for the photoinitiator being used for from about 5 to about 400 seconds, in other embodiments, from about 5 seconds to about 350 seconds, in other embodiments, from about 5 seconds to about 300 seconds, in other embodiments, from about 5 seconds to about 200 seconds, in other embodiments, from about 30 seconds to about 500 seconds, in other embodiments, from about 60 seconds to about 500 seconds, in other embodiments, from about 120 seconds to about 500 seconds, and in other embodiments, from about 200 seconds to about 500 seconds.

In various embodiments of the first aspect of the present invention, the method my also include seeding the bioactive peptide loaded PPF tissue scaffolds of the present invention with cells and then growing those cells on said tissue scaffold using conventional methods. In various embodiments, suitable cells may include, without limitation, endothelial cells, osteocytes, mesenchymal stem cells, or osteoblasts.

In a second aspect, the present invention is directed to a method of post-production functionalization of a 3-D printed poly(propylene fumarate) polymer structure with bioactive peptides. As set for above, if the bioactive peptides are added before the PPF structure is printed and/or cured the peptide are most often damaged by the printing process or the heat of the exothermic crosslinking reaction during the curing process. These problems are avoided in the present process because the bioactive peptides are added well after the PPF structure is printed and cured and are not damaged by the thiol-ene "click" reaction used to attach them to the printed PPF structure.

In these embodiments, a 3-D printable resin comprising a poly(propylene fumarate) polymer having alkene functional groups is prepared as set forth above. Next, a 3-D printed a PPF polymer structure is printed from a 3-D printable resin as set forth above. As will be appreciated, there are alkene functional groups exposed on the surface of the printed PPF polymer structure. A buffered solution is then prepared containing a bioactive peptide having at least one thiol functional group at or near the end terminus, and in some embodiments, a photoinitiator, as set forth above. Finally, the peptide solution is brought into contact with the 3D printed PPF polymer structure to allow the thiol functional group on the bioactive peptides to react with the alkene functional groups on the surface of 3D printed PPF polymer structure thereby tethering the bioactive peptides to the 3D printed PPF polymer structure, as described above. In some embodiments, 3D printed PPF polymer structure is immersed in the buffered peptide solution for from about 5 seconds to about 500 seconds to allow the bioactive peptides to be attached to the 3D printed PPF polymer structure, via the thiol-ene click reaction, as described above.

As set forth above, in some other embodiments, the peptide solution will also contain a photoinitiator, as described above. In these embodiments, the 3D printed PPF polymer structure is irradiated with ultraviolet light at a wavelength known to cause the photoinitiator to produce radicals that speed up the thiol-ene click reactions tethering the bioactive peptides to the 3D printed PPF polymer structure, as described more fully above.

In a third aspect, the present invention is directed to a bioactive peptide loaded PPF tissue scaffold formed from a 3-D printable PPF resin according to the method described above and comprising a PPF polymer matrix and a plurality of bioactive peptides or other bioactive compounds tethered to said PPF polymer matrix by thiol-ene bonds. In some of these embodiments, the bioactive peptide loaded poly(propylene fumarate) tissue scaffold may further comprise one or more additives, which may include, photoinitiators, dyes, light attenuating agents, dispersants, emulsifiers, ceramics, bioglass, hydroxyapatite, J-tricalcium phosphate, crosslinkers and/or solvents, as described above.

In one or more of these embodiments, the bioactive peptide of the bioactive peptide loaded PPF tissue scaffold of the present invention is an angiogenic peptide, osteogenic peptide, or antimicrobial peptide, as described above. In some of these embodiments, the bioactive peptide is selected from the group consisting of basic fibroblast growth factor (bFGF) (CYKRSRYT (SEQ. ID NO. 1)), Bone Morphogenetic Protein 2 (BMP-2) (CKIPKASSVPTELSAISTLYL (SEQ. ID NO. 2)), Osteogenic Growth Peptide (OGP) 10-14 (YGFGG) (SEQ. ID NO. 3), BMP-2 73-92 (KIPKASSVPTELSAISTLYL) (SEQ. ID NO. 4), BMP-7 89-117 (TVPKPSSAPTQLNAISTLYF) (SEQ. ID NO. 5), BMP-9 68-87 (KVGKASSVPTKLSPISILYK) (SEQ. ID NO. 6) and combinations thereof.

In some of these embodiments, the bioactive peptide loaded PPF tissue scaffold of the present invention further comprises a plurality of cells adhered to the bioactive peptide loaded PPF tissue scaffold. In various embodiments, these cells may be of endothelial cells, osteocytes, mesenchymal stem cells, and/or osteoblasts, as described above.

In one or more of these embodiments, the bioactive peptide loaded PPF tissue scaffold of the present invention comprises a 3D printed PPF polymer matrix to which one or more angiogenic peptides and one or more osteogenic peptides have been attached as set forth above. In one or more of these embodiments, the bioactive peptide loaded PPF tissue scaffold of the present invention comprises a 3D printed PPF polymer matrix to which one or more angiogenic peptides and one or more osteogenic peptides have been attached. In one or more of these embodiments, the bioactive peptide loaded PPF tissue scaffold of the present invention comprises a 3D printed PPF polymer matrix to which bFGF (basic fibroblast growth factor) (CYKRSRYT) (SEQ. ID NO. 1) and BMP-2 (bone morphogenetic protein 2) (CKIPKASSVPTELSAISTLYL (SEQ. ID NO. 2)) have been attached. In some of these embodiments, these bFGF and BMP-2 loaded PPF tissue scaffolds may further comprise one or more osteocytes and/or one or more endothelial cells.

In another aspect, the present invention is directed to a method growing cells of a desired type on the bioactive peptide loaded PPF tissue scaffold described above using cell differentiation. In these embodiments, a bioactive peptide loaded PPF tissue scaffold is formed as set forth above using one or more peptides or other bioactive compound known to cause certain stem cells to differentiate into a desired cell type and then seeded with the appropriate type of stem or other cell known to differentiate into the desired cell type in the presence of the one or more peptides or other bioactive compound loaded into the PPF tissue scaffold.

An example of this method is shown in FIG. 1 and further described in Examples 7-12. In the embodiment shown in FIG. 1, a 3D printed PPF polymer matrix with bFGF (basic fibroblast growth factor) (CYKRSRYT) (SEQ. ID NO. 0. 1) and BMP-2 (bone morphogenetic protein 2) (CKIPKASSVPTELSAISTLYL (SEQ. ID NO. 2)) is prepared and then loaded with mesenchymal stem cells (MSCs) as set forth above. As set forth above, bFGF (basic fibroblast growth factor) (CYKRSRYT) (SEQ. ID NO. 1) is known to be involved in angiogenesis and induces MSCs differentiation into endothelial cells and BMP-2 (bone morphogenetic protein 2) (CKIPKASSVPTELSAISTLYL (SEQ. ID NO. 2)) has been shown to induce the mitogenesis of MSCs and their differentiation into osteoblasts. As the MSCs in these embodiments grow, they are acted upon by the bFGF and BMP-2 peptides, which cause them to differentiate into mdothelial cells or osteocytes.

In another aspect, the present invention is directed to a method of repairing a bone defect using the bioactive peptide loaded PPF tissue scaffolds described above. In these methods, a bone defect in a patient that is in need of repair is identified and a determination made whether repair of the will require the peptide loaded PPF tissue scaffold of the present invention. As used herein, a "bone defect" and "defect in a bone" are used interchangeably to refer to an orthotopic defect in a bone that will not heal without intervention. In these embodiments, the repair of the bone defect will be understood to require growth or regrowth of bone and/or other tissue. In these embodiments, a bioactive peptide loaded PPF tissue scaffold loaded with bioactive peptides known to stimulate or facilitate bone growth and sized to fit within said bone defect is prepared as described above and then surgically inserted into the bone defect to stimulate bone growth and, in some embodiments, provide additional support.

In some of these embodiments, the bioactive peptide loaded poly(propylene fumarate) tissue scaffold may be prepared as follows. A 3-D printable resin comprising a poly(propylene fumarate) polymer having alkene functional groups is prepared as set forth above. The precise size and, in some embodiments, the three dimensional shape of the bone defect is determined by conventional means, including, but not limited to magnetic resonance imaging, x-ray imaging, and physical examination and mapped using suitable 3D computer assisted drafting (CAD) software. A CAD or other similar computer file readable by the 3D printer is then prepared providing the necessary data to permit a 3D printer to print a 3D structure sized to fit with the bone defect and then transferred to a 3D printer. Based upon this data, a PPF polymer structure sized to fit within bone defect from a 3-D printable resin. As set forth above, alkene functional groups are exposed and available for bonding only on the surface of the printed PPF polymer structure. The printed PPF polymer structure is then cured and washed to remove any remaining DEF as described above. Finally, the bioactive peptides known to stimulate and/or facilitate bone growth or regrowth are attached via thiol-ene bonds as described above. In various embodiments, bioactive peptide may be an angiogenic peptide, osteogenic peptide, and/or antimicrobial peptide, as described above.

In these embodiments, the peptide loaded PPF tissue scaffold described above is then surgically inserted into the selected bone defect to allow patient's bone to regrow in the bone defect using the bioactive peptide loaded PPF tissue scaffold of the present invention.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials

Fmoc-protected amino acids were purchased from Novabiochem (San Diego, CA). All the solvents were purchased from Sigma-Aldrich (St. Louis, MO), and they were all reagent grade and used as received unless otherwise stated.

Statistics

All quantitative data is presented as an average±standard deviation. Statistical comparisons were performed by ANOVA using JMP software. Significant difference is defined as p<0.05.

Example 1

Synthesis of Peptide Sequences

OGP 10-14 (YGFGG) (SEQ. ID NO. 3), BMP-2 73-92 (KIPKASSVPTELSAISTLYL (SEQ. ID NO. 4)), BMP-7 89-117 (TVPKPSSAPTQLNAISTLYF) (SEQ. ID NO. 5), and BMP-9 68-87 (KVGKASSVPTKLSPISILYK) (SEQ. ID NO. 5) were prepared by Fmoc solid-state peptide synthesis using a Liberty 1 peptide synthesizer (CEM Corporation, Matthews, NC). Briefly, 0.25 mmol of Wang resin containing the appropriate C-terminal amino acid of the sequence was loaded in the synthesizer and subjected to various deprotection and coupling steps under microwave irradiation to yield the target peptide. The resin was then transferred to a peptide synthesis reaction vessel for the following step.

Example 2

Fabrication of the PPF Slides and Scaffolds

PPF was synthesized via a ring opening method, as shown in international (PCT) patent application number PCT/US2015/061314, published as WO 2016/018587, the disclosure of which is incorporated herein by reference in its entirety. The initial PPF resin was stored with only the PPF polymer and a diethyl fumarate (DEF) solvent (Sigma-Aldrich, St. Louis, MO) at a polymer:solvent ratio of 3:1 poly(propylene fumarate):diethyl fumarate (PPF:DEF). This initial PPF resin was then diluted to a 1:1 PPF:DEF ratio using additional DEF to begin the preparation of resin to be cured as thin films or 3D printed. The following photoinitiators and dyes were mixed and dispersed homogenously into the resin to create optimal material flow and photocrosslinking: Irgacure 819/BAPO (BASF, Florham Park, NJ) (0.7% w/w %/o), Oxybenzone/2-Hydroxy-4-methoxybenzophenone (Sigma-Aldrich) (0.4% w/w %), and Irgacure 784 (BASF) (0.3% w/w %/o). PPF thin films were created by placing 6-7 drops of resin between two glass microscope slides. The slides were then placed into a 3D Systems (Rock Hill, SC) ProCure™ UV box for 30 min to promote enough cross-linking to allow samples to be cut into 1 cm×1 cm squares. After cutting, samples were placed back into the UV box for 7.5 hours to ensure complete cross-linking of the polymer.

3D printed porous cylindrical scaffolds with Schoen Gyroid triply periodic minimal surface were fabricated with dimensions of 6 mm diameter and 5 mm height, using the same resin chemistry to validate the optimized media regime on the 3D scaffolds. This pore geometry included a strut diameter of 187.5 μm, pore diameter of 625 μm, pore surface area of 342.27 $mm^2$ and pore volume of 17.77 $mm^3$ of PPF. A computer aided design (CAD) file of these features was created using SolidWorks software (Dassault Systèmes, Waltham, MA) and 3D printing was performed in an EnvisionTEC Perfactory® (Dearborn, MI) P3 3D printer. To remove the uncured resin from the cross-linked polymer, washing was performed using 70% acetone (VWR, Radnor, PA) and Phosphate Buffered Saline (PBS) (Life Technologies).

Example 3

Peptide Synthesis

Figure 2:
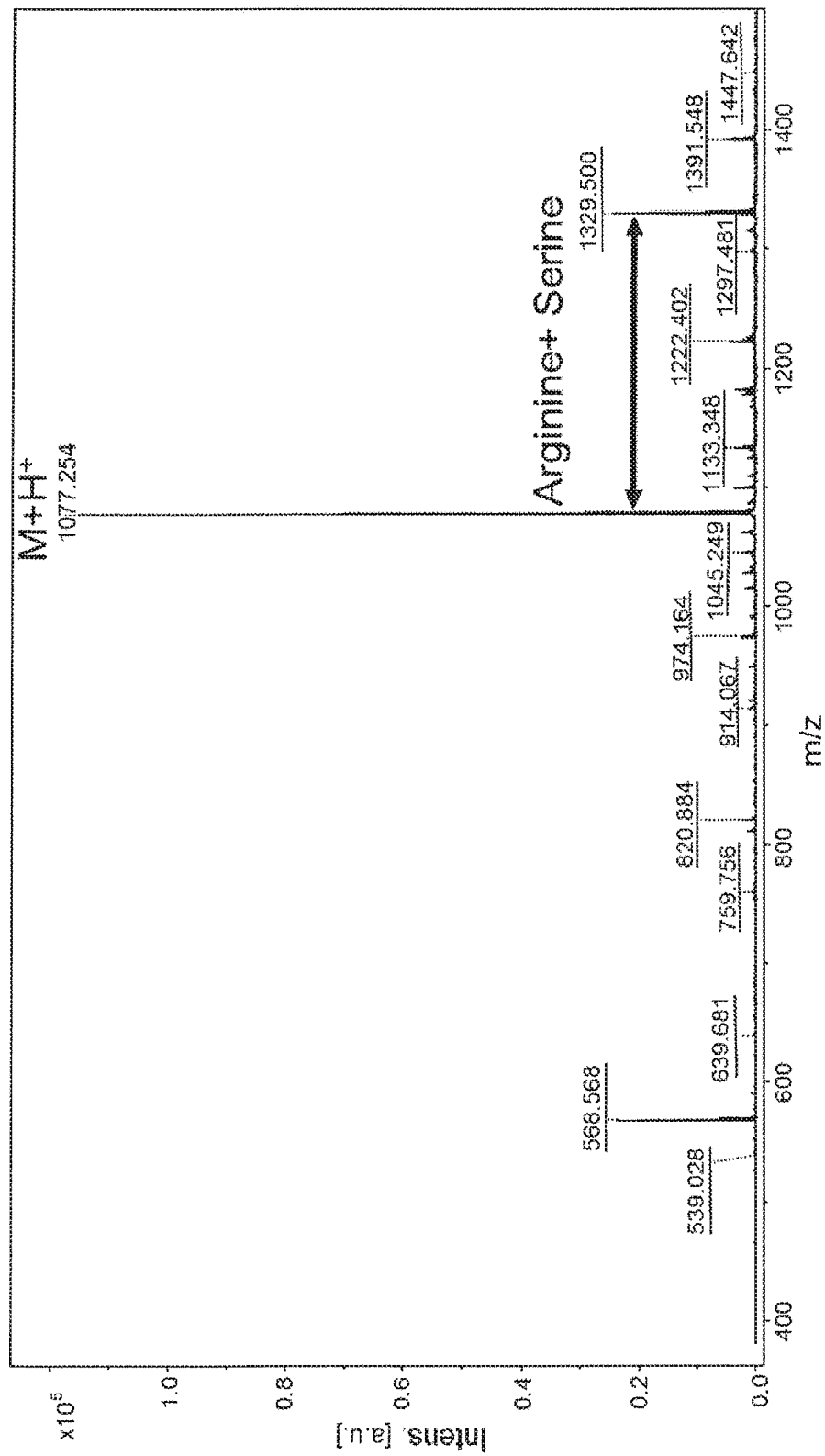
FIG. 2 is a MALDI spectrum of a bFGF peptide (CYKRSRYT) (SEQ. ID NO. 1) Cleavage cocktail: TFA/phenol/DI water/TIPS=88/5/5/2; Cleavage time: 4 hours.
Figure 3:
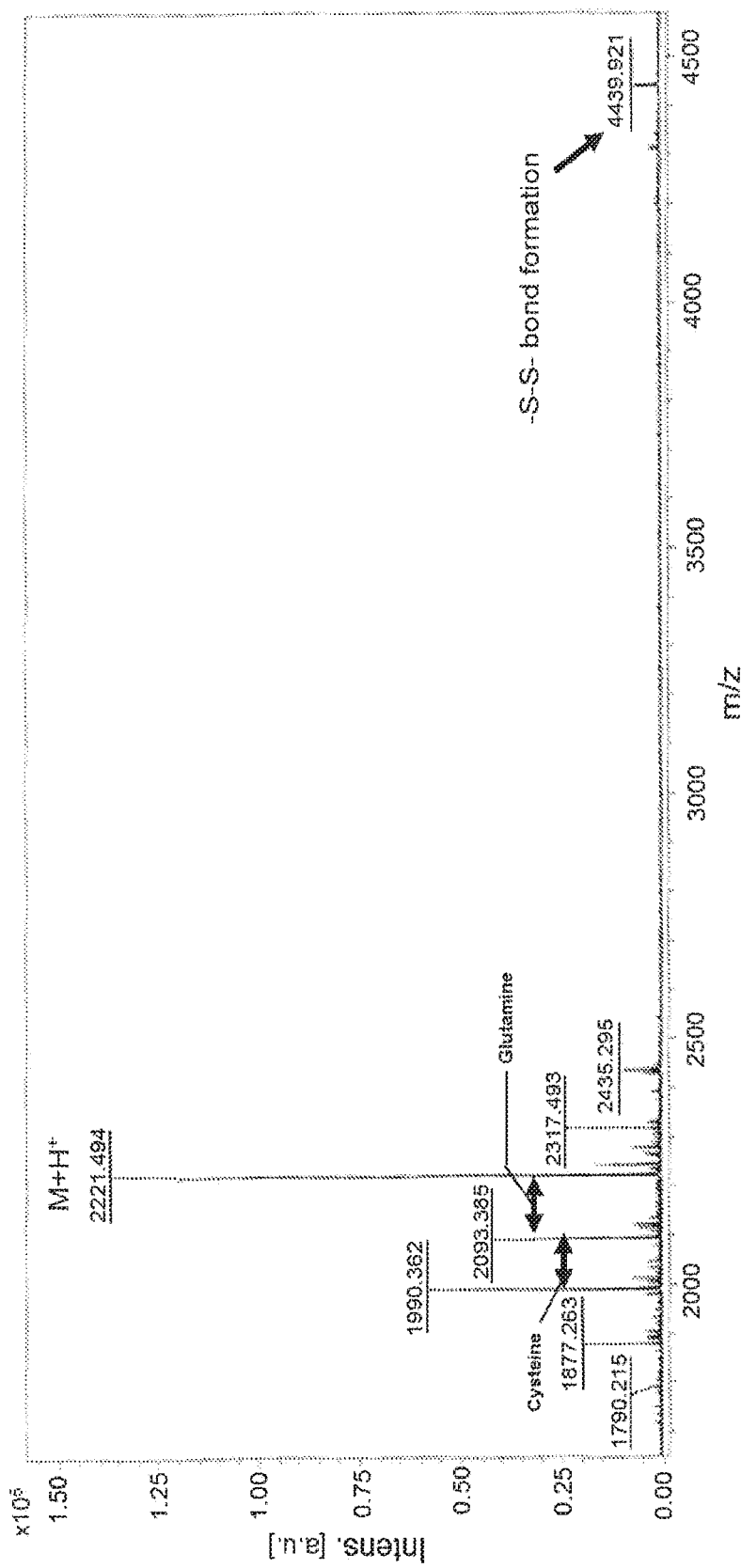
FIG. 3 is a MALDI spectrum of BMP-2 peptide (CK-IPKASSVPTELSAISTLYL) (SEQ. ID NO. 2). Cleavage cocktail: TFA/phenol/DI water/TIPS=88/5/5/2; Cleavage time: 2 hours.
Figure 4A:
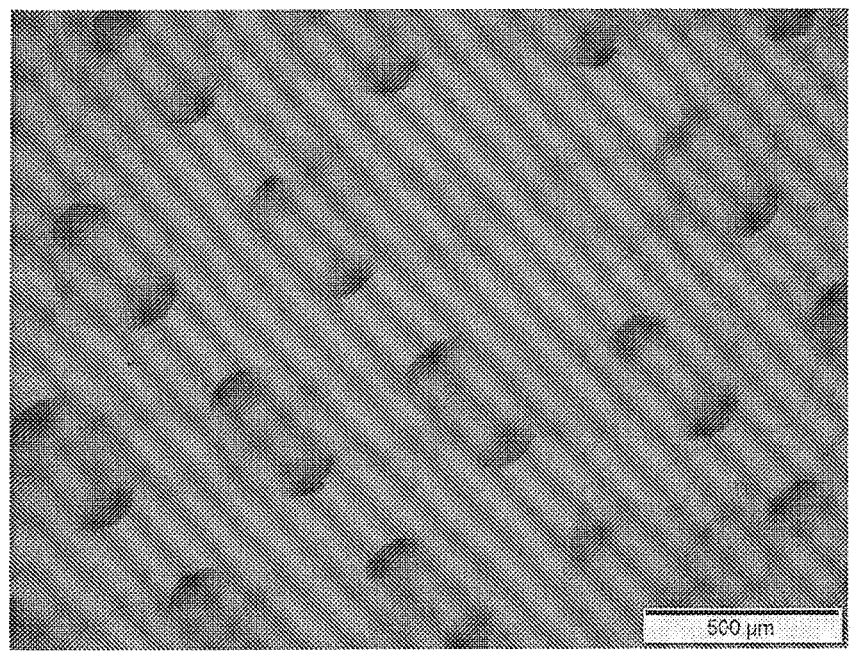
FIGS. 4A-C are images of a PPF polymer matrix showing the matrix: after physical adsorption or a FITC-PEG-thiol dye (Mean Intensity: 934.88±91.76) (FIG. 4B) and after the thiol-ene click reaction between the PPF polymer in the matrix and the FITC-PEG-thiol dye (Mean Intensity: 891.17±65.41) (FIG. 4A).
Figure 4B:
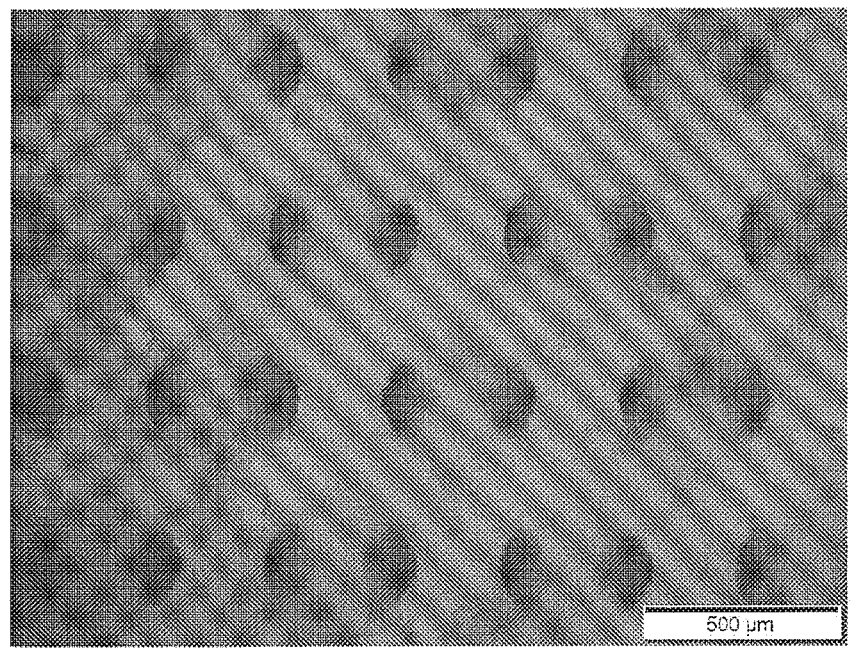
Figure 4C:
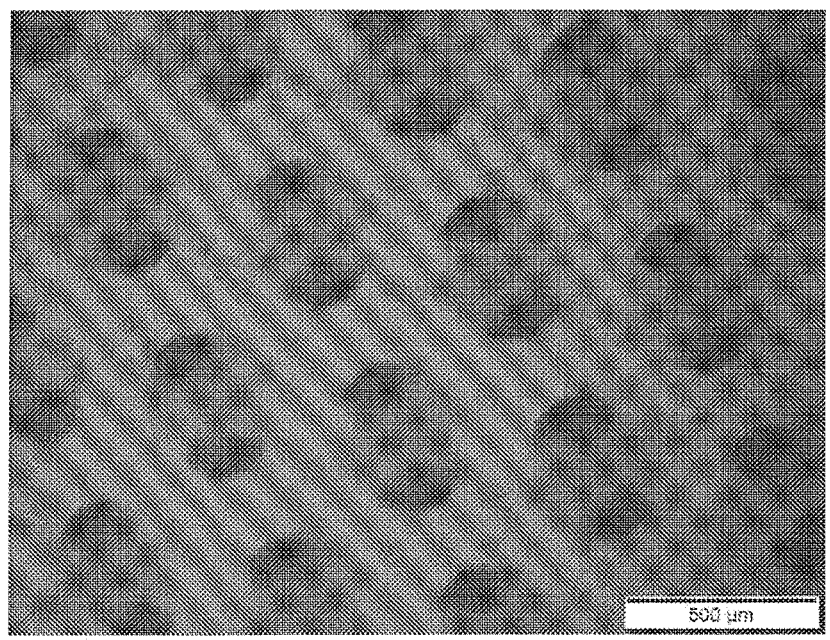
Figure 5A:
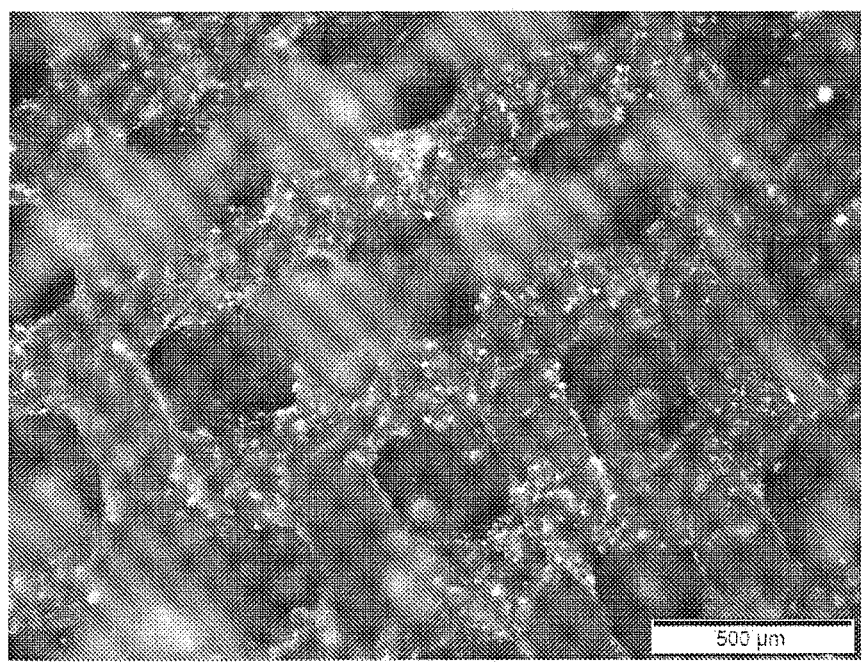
FIGS. 5A-B are images showing cell distribution within a bioactive peptide loaded poly(propylene fumarate) tissue scaffold according to one or more embodiments of the present invention. Cell type: hMSCs P5. Original cell seeding density: 2.5*10$^5$ cells/scaffold. Time point: 24 hr after cell seeding with live cell tracker CM-Dil.
Figure 5B:
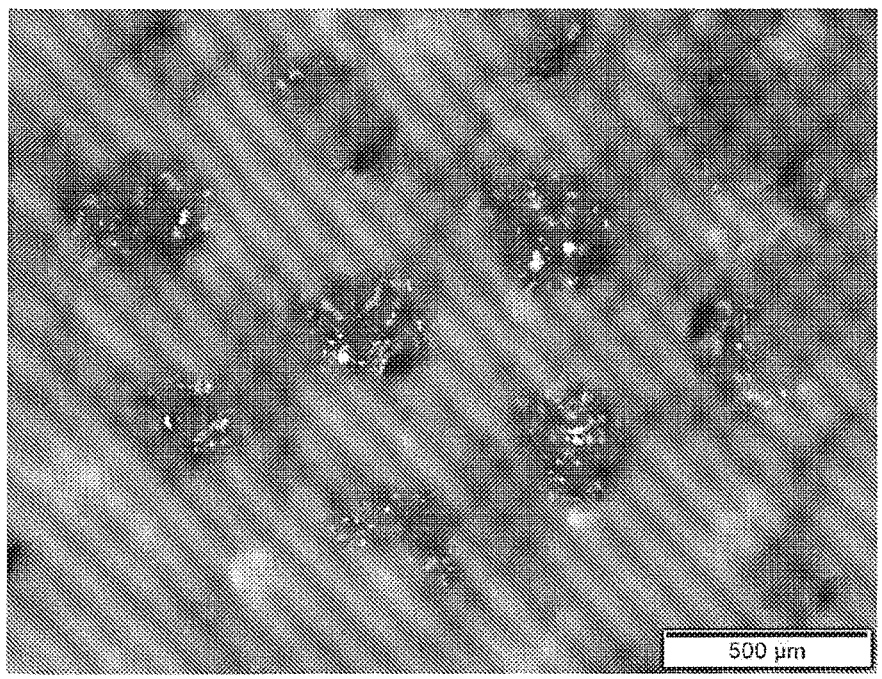
Figure 6A:
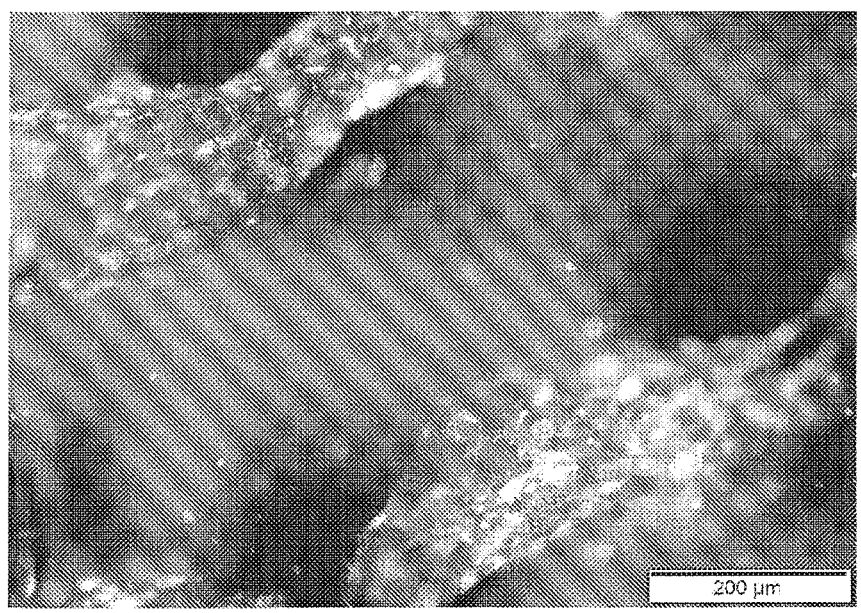
FIGS. 6A-C are images showing cell distribution within a bioactive peptide loaded poly(propylene fumarate) tissue scaffold according to one or more embodiments of the present invention showing substantially homogeneous distribution on cell surface.
Figure 6B:
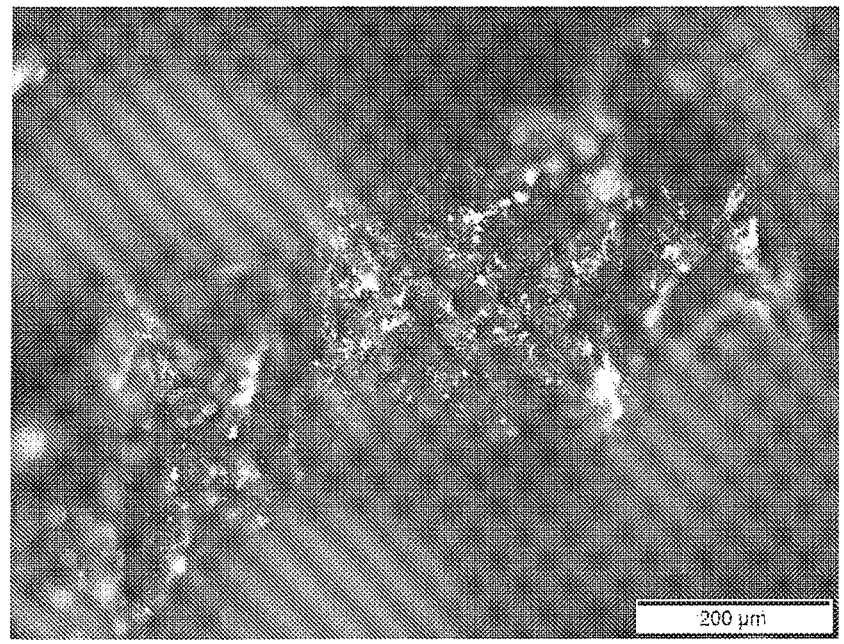
Figure 6C:
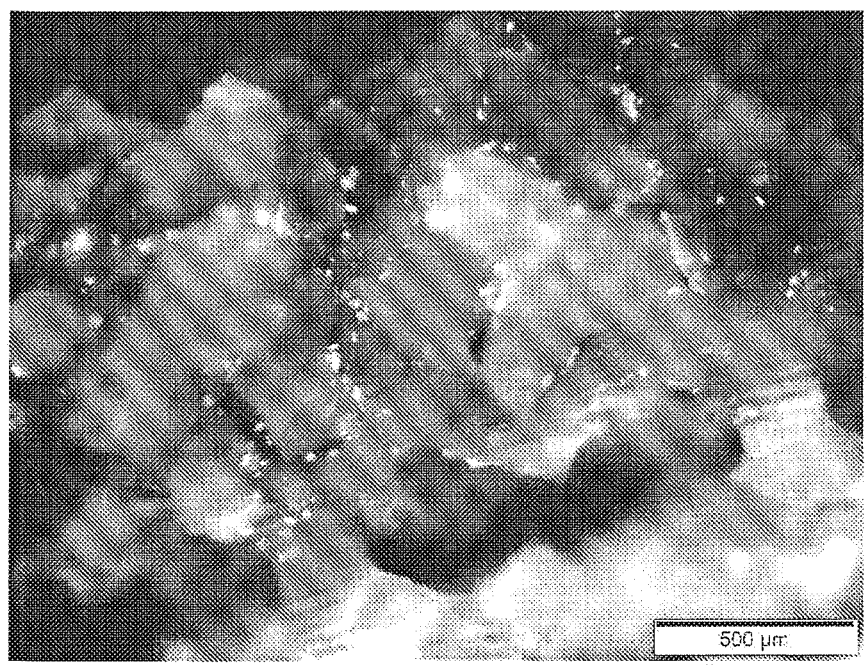
Figure 7:
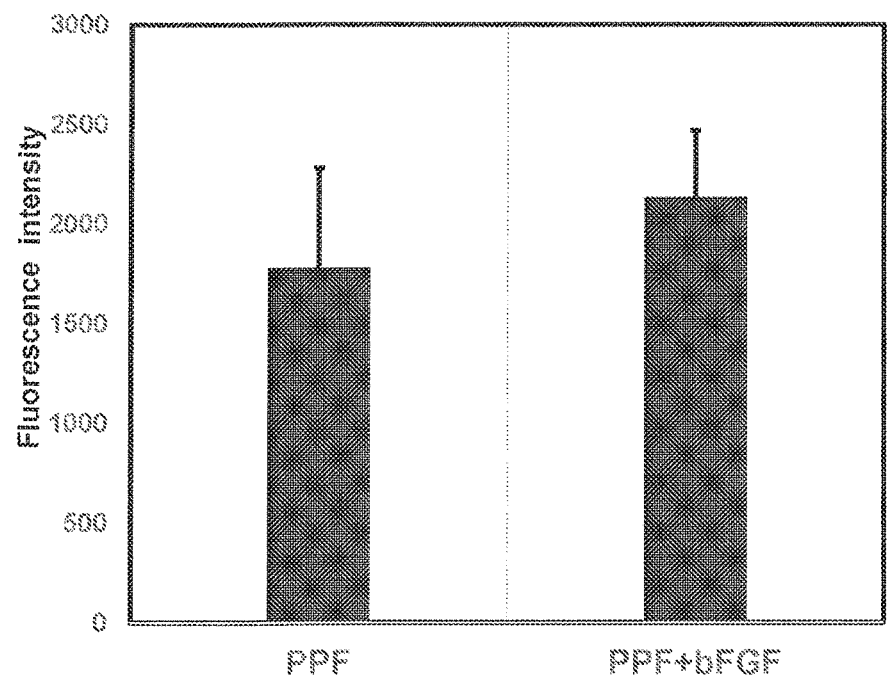
FIG. 7 is a graph showing the results of cell adhesion tests done on PPF thin films. Cell type: hMSCs P5. Cell original seeding density: 198 cells/mm$^2$ (same for scaffold). Time: 48 hr after cell seeding. Control: cells cultured in well plate. Thin films thickness: 100-150 μm. Click reaction: bFGF (1 hour under UV). Plates were coated with Poly-HEMA first to ensure cell adhesion on thin film.
Figure 8A:
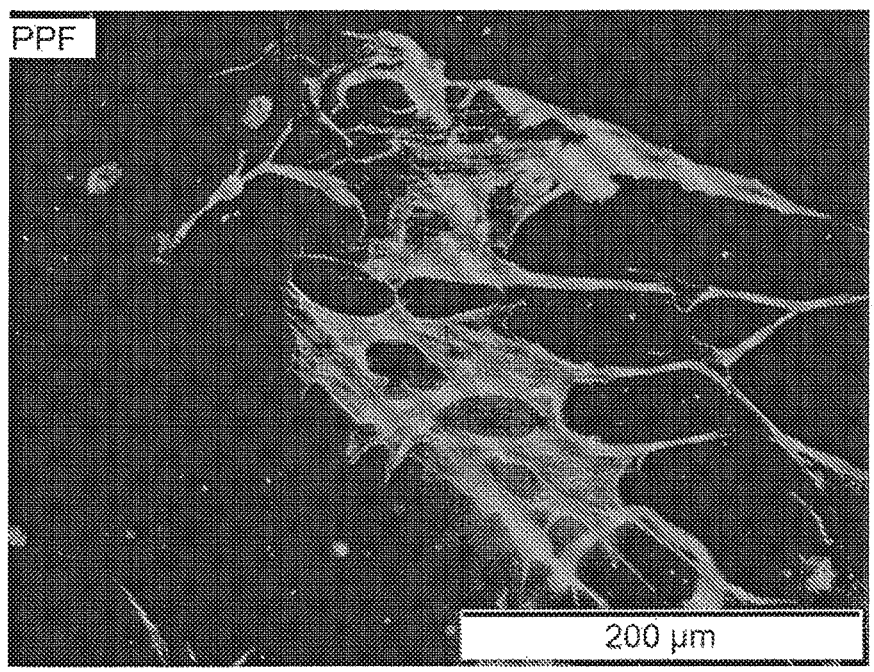
FIGS. 8A-B are images showing the results of cell spreading experiments.
Figure 8B:
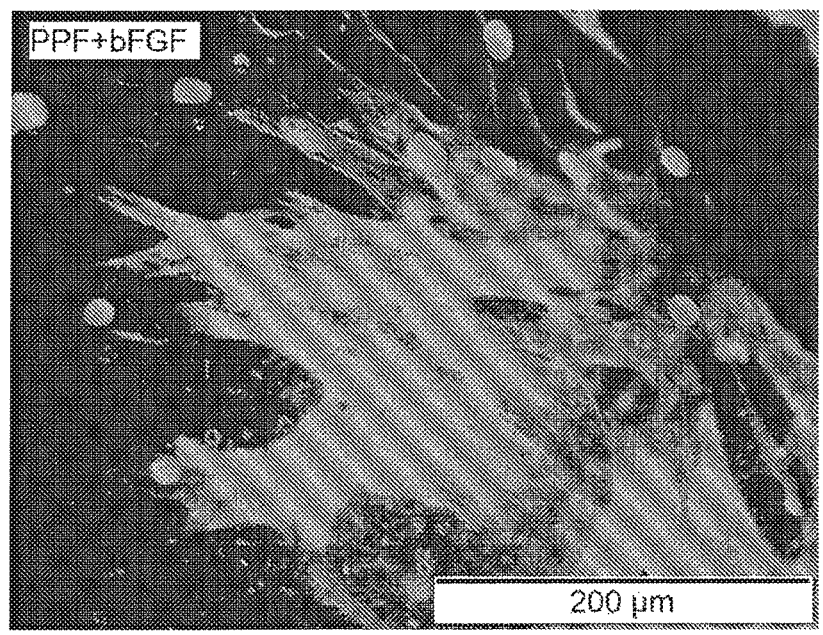
Figure 9:
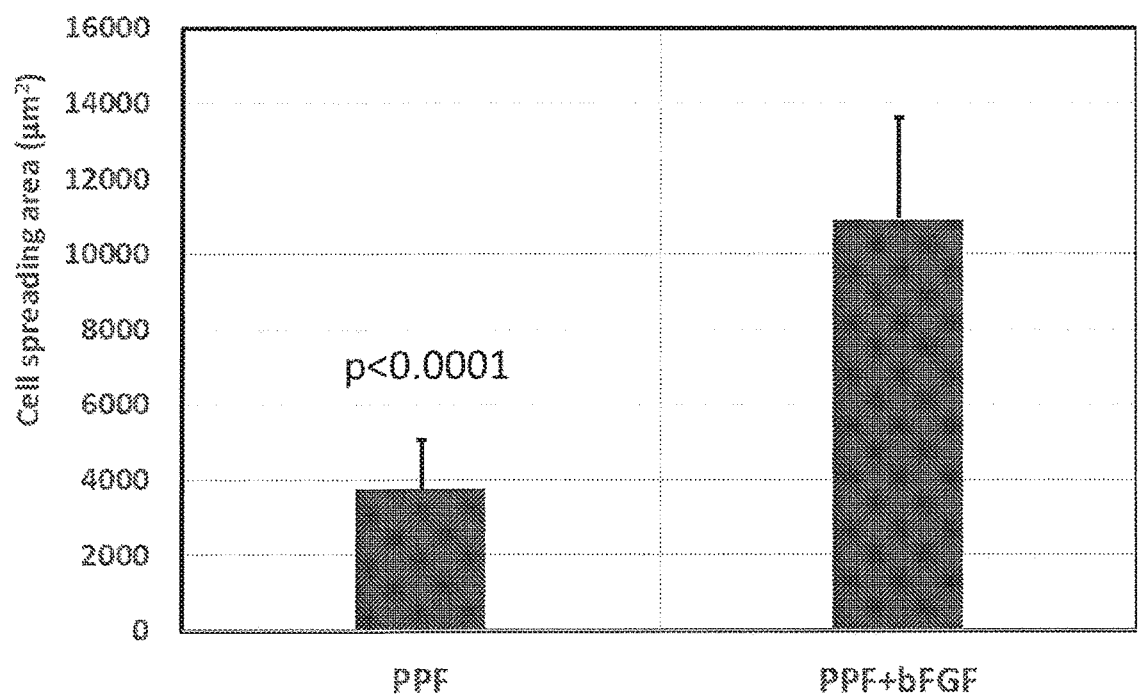
FIG. 9 is a graph showing the results of cell spreading experiments comparing cell spreading on PPF polymer films and PPF polymer films functionalized with bFGF according to one or more embodiments of the present invention. 10 sections were randomly picked and used for cell spreading area calculation.
Figure 10:
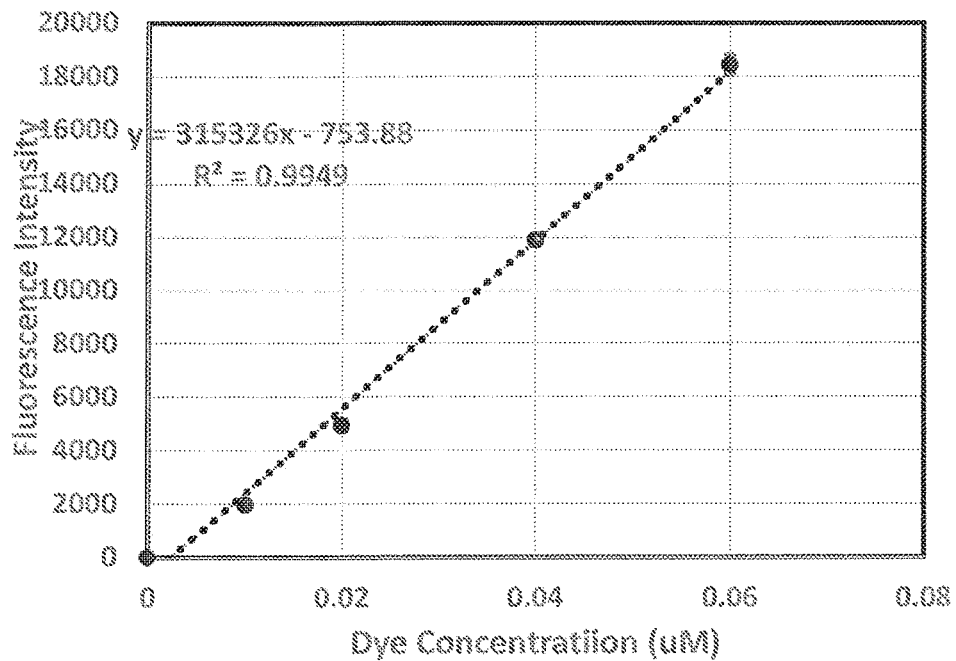
FIG. 10 is a calibration curve showing fluorescence Intensity as a function of FITC-PEG-thiol dye concentration after 1 hour exposure to ultraviolet light.
Figure 11:
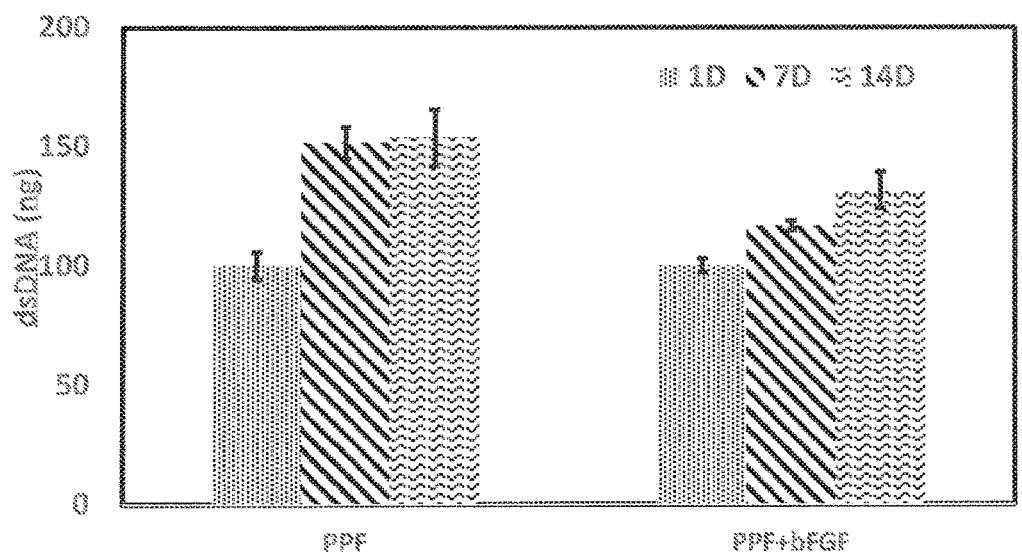
FIG. 11 is graph showing cell proliferation results taken at 1, 7, and 14 days for a PPF polymer matrix and a PPF polymer matrix functionalized with bFGF according to one or more embodiments of the present invention. Cell type: hMSCs P5. Original cell seeding density: 2.5*10$^5$ cells/scaffold. Cell proliferation using Cyquant assay.

The peptides were synthesized using standard solid phase FMOC chemistry on a Liberty 1 peptide microwave synthesizer (CEM Cooperation, Matthews, NC). FMOC-protected amino acids was synthesized and coupled onto the bioactive peptide sequences as the spacer. For both thiol-functional basic fibroblast growth factor (bFGF) peptide (CYKRSRYT (SEQ. ID NO. 1)) and bone morphogenetic protein 2 (BMP-2) peptide (CKIPKASSVPTELSAISTLYL (SEQ. ID NO. 2)), amino acid cysteine was added to the N terminus following standard FMOC conditions. MALDI-T of MS: bFGF-thiol peptide, $[M+H]^+$ m/z calculated to be 1077.24, found at 1077.254 (See FIG. 2); BMP2-thiol peptide, $[M+H]^+$ m/z calculated to be 2221.21, found at 2221.494 (See FIG. 3).

Example 4

2.4 Fabrication of Porous 3D Scaffolds

The 3D scaffolds were printed using an Envision TEC (Dearborn, MI) Perfactory 3 which was calibrated to produce a UV mask with a nominal irradiance at 350 $mWdm^{-2}$.

Example 5

Conjugation of Peptide onto Scaffolds by Thiol-Ene Reaction bFGF-thiol or BMP-2-thiol peptides (1 μM) were dissolved in PBS/DMF mixture (PBS/DMF=100:1, v/v) with Irgacure 2959 (0.5 µM) as the photoinitiator. The 3D printed scaffold was immersed in the peptide solutions and treated with UV (254 nm) for 1 hr at room temperature. The scaffold was then washed with methanol, ethanol and PBS three times for each and blown dry prior for characterization and biological test.

Example 6

Characterization of Peptide-Conjugated Scaffolds

The structure of 3D printed PPF scaffold was characterized nondestructively using X-ray micro-computed tomography (µ-CT, Skyscan 1172). The 3D scanning of scaffold was carried out using the following parameters: 60 kV voltage, no filter, medium camera, camera exposure preset time of 30 ms and resolution of 10.0 µm.

Calculation: bonded peptide via click reaction; Scaffold surface: 1266 mm$^2$ (according to the micro-CT result); Physical adsorption: 0.79 picomole/cm$^2$; Click reaction: 52.45 picomole/cm$^2$ (0.05 µM dye+0.05 µM initiator); 78.52 picomole/cm$^2$ (0.1 µM dye+0.05 µM initiator)

Example 7

Human Mesenchymal Stem Cell (hMSCs) Culture and Seeding into 3D Printed Scaffold Female hMSCs (Lonza. Wakersville, MD) were cultured following manufacturer's protocol using Lonza MSCs growth medium (supplied with 10 vol % of FBS, 10 mL L-glutamine, 30 µg/mL Gentamicin, and 15 ng/mL: Amphotericin) without any osteogenic additives to avoid MSCs differentiation. hMSCs within passage 3-5 were used for cell seeding within 3D printed PPF scaffolds with or without peptide functionalization and growth medium was changed every other day. (See FIGS. 4A-C, 5A-B, and 6A.-C)

Example 8 hMSCs Survival and Proliferation In Vitro

Cell proliferation capability within peptide functionalized or non-functionalized scaffolds was detected and quantified using CyQUANT cell proliferation assay kit (Invitrogen) following the manufacturer's protocol 1, 14 and 28 days after cell seeding. In brief, cell growth medium was aspirated and samples were frozen and thawed at r.t. before adding CyQUANT GR dye/cell-lysis buffer mixture (1 mL/sample). After vortexing and incubation in the mixture for 10 minutes protected from light, sample supernatant fluorescence was measured using a fluorescence microplate reader with the excitation at ~480 nm and emission at ~520 nm. A calibration curve was obtained using standard DNA at the concentrations of 0, 10, 50, 100, 200, 400, 600, 800 and 1000 ng/mL. N=3 replicates were studied for each group, and each sample was tested three times to eliminate pipet error. (See FIGS. 7, 8A-B, 9, 10, 11)

Example 9 hMSCs Osteogenic or Endothelial Differentiation In Vitro: Real Time Reverse Transcription Polymerase Chain Reaction (RT-PCR)

Figure 12:
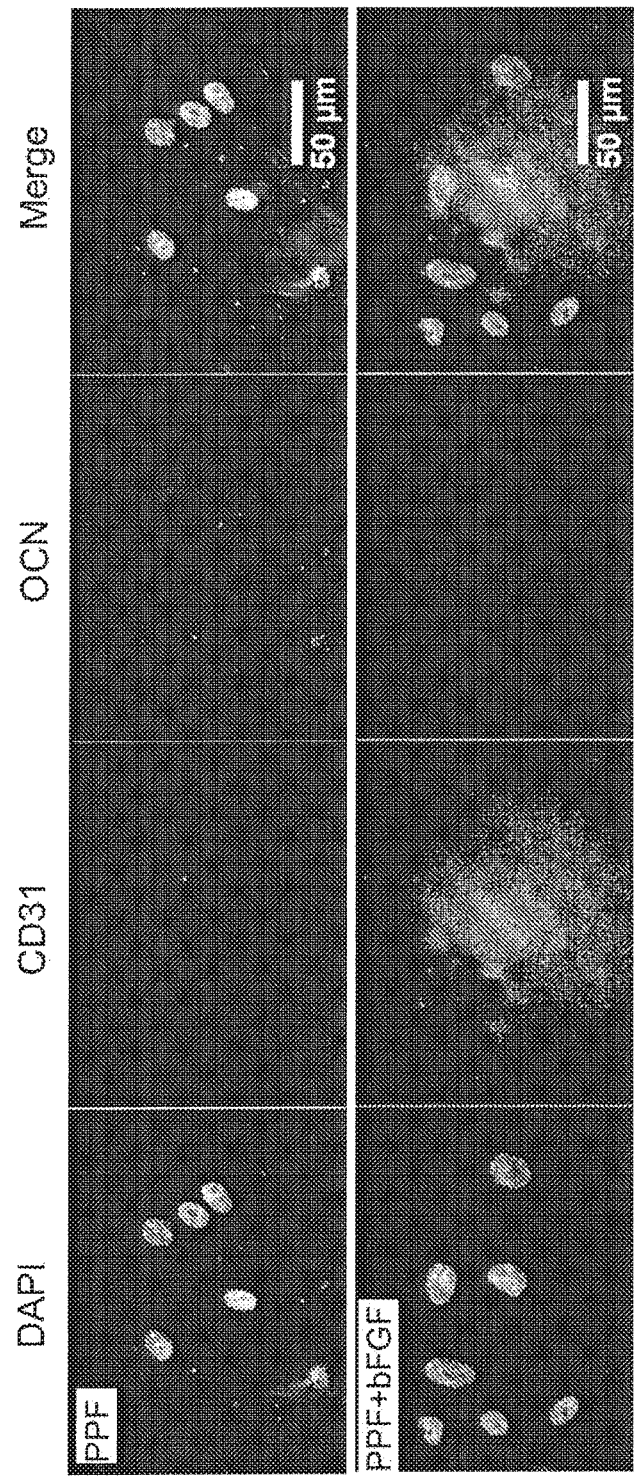
FIG. 12 is a schematic containing images comparing the results of cell differentiation tests done on PPF polymer films and PPF polymer films functionalized with bFGF according to one or more embodiments of the present invention. Cell type: hMSCs P5. Cell original seeding density: 198 cells/mm$^2$ (same for scaffold). Time: 2 weeks after cell seeding. Thin films thickness: 100-150 μm. Plates were coated with Poly-HEMA first to ensure cell adhesion on thin film.
Figure 13A:
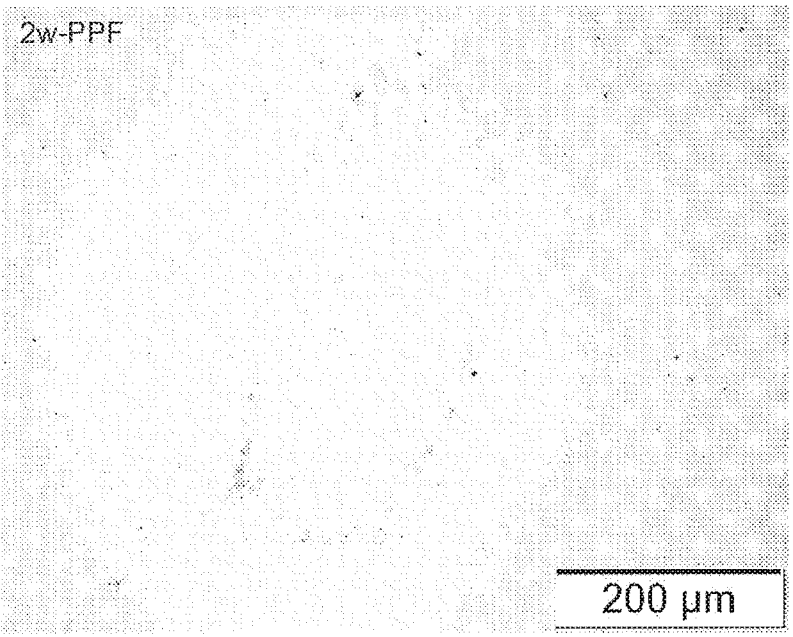
FIGS. 13A-D are images showing alizarin Red S. staining of 3-D printed PPF scaffolds (2w-PPF) (FIG. 13A-B); 2w-PPF+bFGF (FIG. 13C); and 4w-PPF+bFGF (FIG. 13D).
Figure 13B:
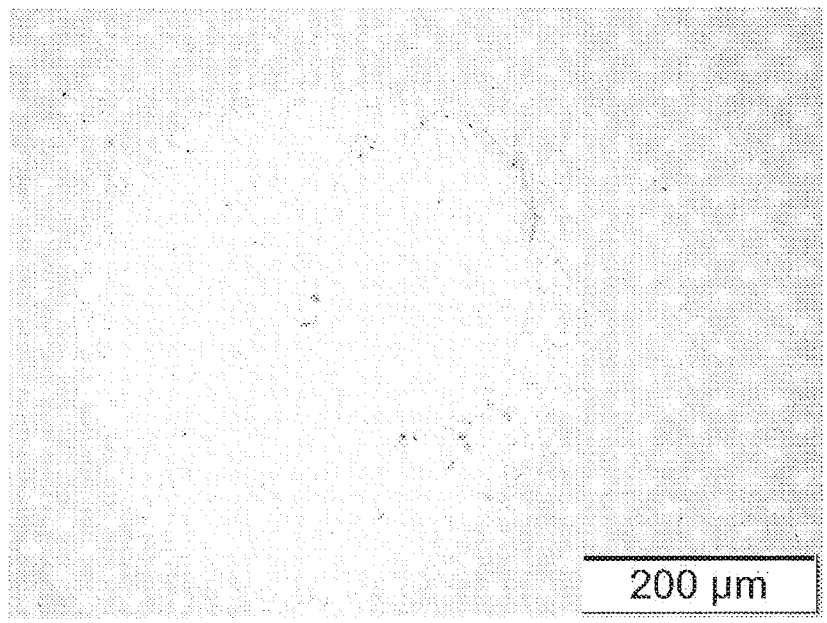
Figure 13C:
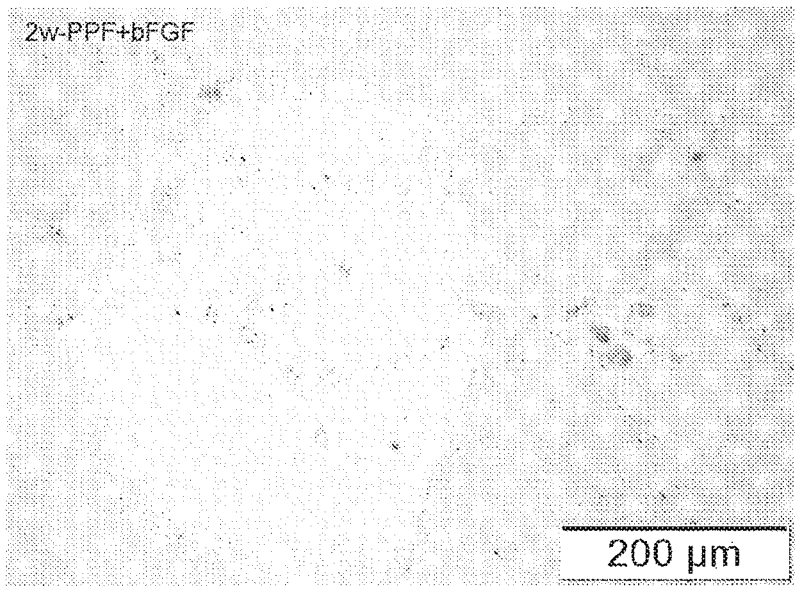
Figure 13D:
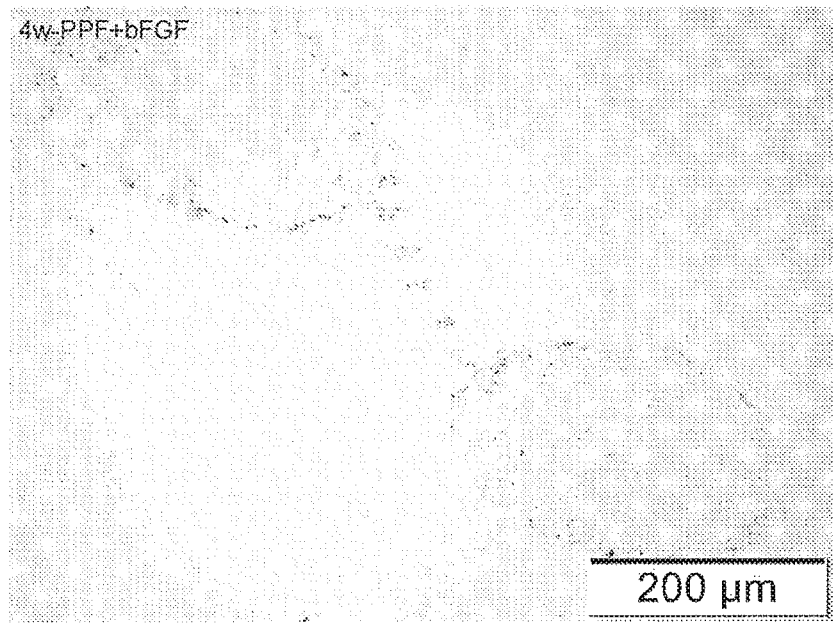
Figure 14:
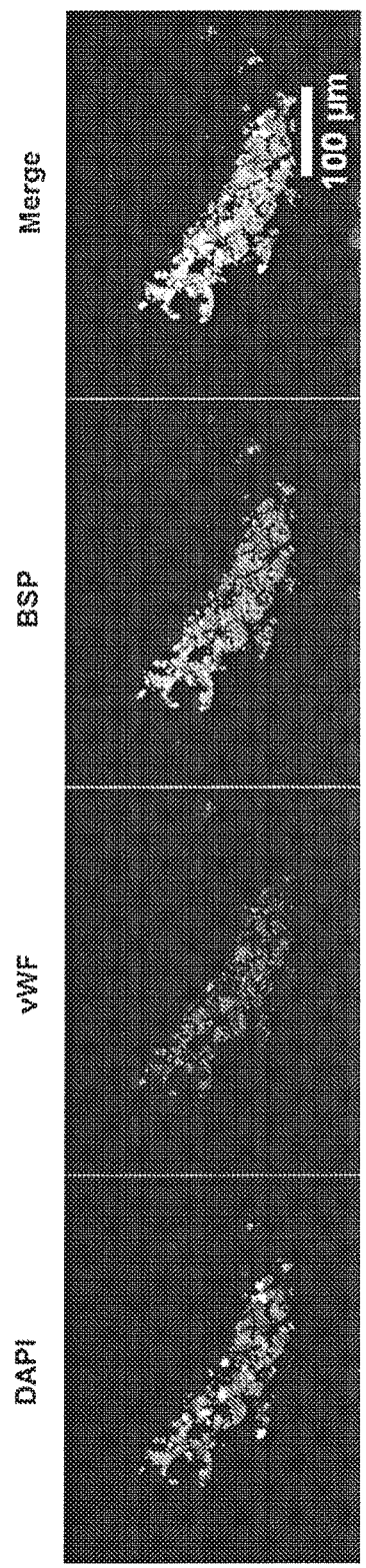
FIG. 14 is a schematic containing images comparing the results of cell differentiation tests done on PPF polymer scaffolds.

RNA extraction and isolation from samples was conducted following the RNeasy Mini kit instructions (Qiagen, Valencia, CA). In brief, cell-seeded 3D printed scaffolds were first homogenized in 600 µL lysis buffer, mixed with ethanol by pipetting and then the mixture was applied to RNeasy Mini Column for total RNA isolation. DNase digestion was performed during the RNA isolation process using Qiagen RNase free DNase set (Qiagen, Valencia, CA). RNA quantity and purity was detected using a Take3Multi-Volume Plate and a Synergy Mx Microplate Reader (BioTek, Winooski VT) at 260 nm. RNA was then reverse transcribed into cDNA using the Taqman Reverse Transcription Reagents kit (Life Technologies, Grand Island, NY) following the manufacturer's protocol. cDNA was stored at −20° C. for further test. Real time RT-PCR was performed with a 7500 Real time PCR System (Applied Biosystems) using SYBR Green Master Mix and designed primers. 10 ng of cDNA, 1×SYBR Green Master Mix, forward and reverse primers (209.4 nM for each) and corresponding amount of DNase/RNase-free water were included in a 100 µL reaction mixture. Glyceraldehyde-3-phosphate dehydrogenase (GAPDH) was used as the housekeeping gene and osteogenic markers Runx2, BSP and OCN as well as endothelial marker CD31 were checked. (See, FIG. 12). All the primer information was listed in Table 1. Gene expressions of normal hMSCs were used as the control and a standard $\Delta\Delta C_t$ method was applied to calculate the fold difference.

TABLE 1

Primers used in real time RT-PCR to detect hMSCs differentiation

| Primer | Sequence |
|---|---|
| hGAPDH | Forward, gacagtcagccgcatctt (SEQ. ID NO. 7)<br>Reverse, ccatggtgtctgagcgatgt (SEQ. ID NO. 8) |
| hRunx2 | Forward, ggacgaggcaagagtttcac (SEQ. ID NO. 9)<br>Reverse, caagcttctgtctgtgccttc (SEQ. ID NO. 10) |
| hBSP | Forward, cctggcacagggtatacagg (SEQ. ID NO. 11)<br>Reverse, ctgcttcgctttcttcgttt (SEQ. ID NO. 12) |
| hOCN | Forward, catgagagccctcac (SEQ. ID NO. 13)<br>Reverse, agagcgacaccctagac (SEQ. ID NO. 14) |
| hCD31 | Forward, tctatgacctcgccctccacaaa (SEQ. ID NO 15)<br>Reverse, gaacggtgtcttcaggttggtatttca (SEQ. ID NO. 16) |

Example 10 hMSCs Osteogenic or Endothelial Differentiation In Vitro: Immunohistochemistry (IHC)

All samples were collected and fixed in 3.7% paraformaldehyde buffer for 2 hours, and then washed with 1×PBS thoroughly before processing in a paraffin processor. The samples were then embedded in paraffin blocks, sectioned into 5 µm slides by microtome and left to dry at 42° C. overnight before staining. For immunohistology staining, samples were first set in a 60° C. oven for 1 hour to obtain a good attachment between sections and slides, and then rehydrated through the following wash steps: xylene (2×2 min), xylene and EtOH mixture (v/v 1:1, 1×2 min), 100% EtOH (2×2 min), 95% EtOH (1×2 min), 70% EtOH (1×2 min), 50% EtOH (1×2 min) and DI water. The samples were first incubated in pepsin reagent for 15 min to expose the antigenic sites. After washing with 1×TBS three times, blocking buffer (10% donkey serum, 0.3% Triton X-100 in 1×PBS) was added and samples were incubated for 1 hour at r.t. to block the non-specific binding. After aspiration, the samples were incubated in primary antibody (bone sialoprotein BSP, v/v 1:200; osteocalcin OCN, v/v 1:100; runt related transcription factor Runx2, v/v 1:100; CD31 v/v 1:100) overnight at 4° C. After washing with 1×TBS three times, samples were stained by incubation in a solution of corresponding secondary antibodies (Alexa Flour 546 Goat for BSP or CD31, v/v 1:200; Alexa Flour 488 Mouse for Runx2 or OCN, v/v 1:200) for 1 hour at r.t. in the dark. The samples were then washed again with 1×TBS three times and stained with DAPI (300 nM in DI water) for nuclei for 15 min at r.t. avoiding light. After washing with 1×TBS three times, samples were mounted and viewed under an IX81 Microscope (Olympus, Center Valley, PA) with mercury bulb excitation and filters of DAPI, FITZ and TRITC. (See, FIG. 12)

Example 11

Biochemistry of hMSCs-Seeded Scaffolds In Vitro

After sectioning and rehydration as mentioned above, freshly prepared Alizarin Red S. solution (2 g in 100 mL ddH$_2$O, pH adjusted to 4.2) was added onto samples. After incubation at r.t. for around 10 min, the Alizarin Red S. solution was carefully removed and samples were thoroughly washed with a series of solvents as followed: 70% EtOH (2×2 min), 95% EtOH (2×2 min), 100% EtOH (2×2 min), and xylene (2×2 min). The sections were then mounted and observed under bright field microscopy (Olympus 1×81, equipped with QImaging Micropublisher 3 camera) for imaging. (See, FIGS. 13A-D, 14)

Example 12

ALP Activity of hMSCs-Seeded Scaffolds In Vitro

The ALP activity of hMSCs-seeded 3D printed PPF scaffolds with or without peptide functionalization was assessed by SensoLyte® pNPP Alkaline Phosphate Assay Kit (Anaspec, Fremont, CA, AS-72146) following the manufacturer's instructions. In brief, 1 mL of 1× assay buffer was added to each sample to lysis the cells within the scaffolds. After thorough vortexing and centrifuge, the supernatant was collected for ALP activities assessment. 50 μL of samples was first mixed with 50 μL of pNPP solution and incubated at r.t. in dark for 1 hr before detecting at the absorbance of 405 nm. The total DNA content of the same sample was detected using CYQUANT assay (following the same approach as mentioned above) to normalize the ALP result. A standard curve of alkaline phosphatase at the concentrations of 0, 3.1, 6.2, 12.5, 25, 50, 100 and 200 ng/mL were used to quantify the ALP amount within samples.

What is claimed is:

1. A method of making a bioactive compound loaded poly(propylene fumarate) tissue scaffold comprising:
   a. preparing a 3-D printable resin comprising a poly(propylene fumarate) polymer having alkene functional groups in its polymer chain;
   b. forming a poly(propylene fumarate) polymer structure from said 3-D printable resin using 3-D printing technology, wherein said poly(propylene fumarate) polymer structure has a surface with exposed alkene functional groups;
   c. preparing a bioactive compound having at least one thiol functional group at or near its terminus selected from the group consisting of basic fibroblast growth factor (bFGF) (CYKRSRYT (SEQ. ID NO. 1)), Bone Morphogenetic Protein 2 (BMP-2) (CKIPKASSVP-TELSAISTLYL (SEQ. ID NO. 2), Osteogenic Growth Peptide (OGP), 10-14 (YGFGG) (SEQ. ID NO. 3), BMP-2 73-92 (KIPKASSVPTELSAISTLYL) (SEQ. ID NO. 4), BMP-7 89-117 (TVPKPSSAPTQLNAISTLYF) (SEQ. ID NO. 5), BMP-9 68-87 (KVGKASSVPTKLSPISILYK) (SEQ. ID NO. 6), and combinations thereof;

d. contacting said poly(propylene fumarate) polymer structure with said bioactive compound; wherein the least one thiol functional group on said bioactive compound reacts with the alkene functional groups in the poly(propylene fumarate) polymer chains exposed on the surface of said poly(propylene fumarate) polymer structure, thereby tethering said bioactive compound to said poly(propylene fumarate) polymer structure to form a bioactive compound loaded tissue scaffold.

2. The method of claim 1 wherein said 3-D printable resin further comprises diethyl fumarate (DEF).

3. The method of claim 1 wherein said 3-D printable resin further comprises at least one of photoinitiators, dyes, light attenuating agents, dispersants, emulsifiers, ceramics, bioglass, hydroxyapatite, β-tricalcium phosphate, and solvents.

4. The method of claim 1 wherein said poly(propylene fumarate) polymer has a number average molecular weight ($M_n$) as measured by size exclusion chromatography or mass spectroscopy of from about 500 g/mole to about 10,000 g/mole.

5. The method of claim 1 wherein said poly(propylene fumarate) polymer has a polydispersity index ($Đ_m$) as measured by size exclusion chromatography of from about 1.0 to about 2.0.

6. The method of claim 1 wherein the poly(propylene fumarate) polymer structure formed in said step of forming (step B) is porous.

7. The method of claim 1 further comprising:
E. seeding the tissue scaffold with cells; and
F. growing said cells on said tissue scaffold.

8. The method of claim 7 wherein said cells are selected from the group consisting of endothelial cells, osteocytes, mesenchymal stem cells, osteoblasts, and combinations thereof.

9. The method of claim 1 wherein said poly(propylene fumarate) polymer has a number average molecular weight ($M_n$) as measured by size exclusion chromatography or mass spectroscopy of from 1000 g/mole to 5000 g/mole.

10. The method of claim 1 wherein said poly(propylene fumarate) polymer has a number average molecular weight ($M_n$) as measured by size exclusion chromatography or mass spectroscopy of from 1000 g/mole to 3000 g/mole.

11. The method of claim 1 wherein said poly(propylene fumarate) polymer has a polydispersity index ($Đ_m$) as measured by size exclusion chromatography of from about 1.05 to about 1.6.

12. The method of claim 1 wherein said poly(propylene fumarate) polymer has a polydispersity index ($Đ_m$) as measured by size exclusion chromatography of from about 1.05 to about 1.2.

* * * * *

SEQUENCE LISTING

```
<160> NUMBER OF SEQ ID NOS: 16

<210> SEQ ID NO 1
<211> LENGTH: 8
<212> TYPE: PRT
<213> ORGANISM: Artificial
<220> FEATURE:
<223> OTHER INFORMATION: Artificially generated sequence for basic
      fibroblast growth factor
<220> FEATURE:
<221> NAME/KEY: misc_feature
<223> OTHER INFORMATION: bFGF (basic Fibroblast Growth Factor)

<400> SEQUENCE: 1

Cys Tyr Lys Arg Ser Arg Tyr Thr
1               5

<210> SEQ ID NO 2
<211> LENGTH: 21
<212> TYPE: PRT
<213> ORGANISM: Artificial
<220> FEATURE:
<223> OTHER INFORMATION: Artificially generated sequence for Bone
      Morphogenic Protein 2

<400> SEQUENCE: 2

Cys Lys Ile Pro Lys Ala Ser Ser Val Pro Thr Glu Leu Ser Ala Ile
1               5                   10                  15

Ser Thr Leu Tyr Leu
            20

<210> SEQ ID NO 3
<211> LENGTH: 5
<212> TYPE: PRT
<213> ORGANISM: Artificial
<220> FEATURE:
```

```
<223> OTHER INFORMATION: Artificially generated sequence containing
      residues 10 through 14 of Osteogenic Growth Peptide (OGP)
<220> FEATURE:
<221> NAME/KEY: misc_feature
<223> OTHER INFORMATION: Residues 10-14 of Osteogenic Growth Peptide
      (OGP)

<400> SEQUENCE: 3

Tyr Gly Phe Gly Gly
1               5

<210> SEQ ID NO 4
<211> LENGTH: 20
<212> TYPE: PRT
<213> ORGANISM: Artificial
<220> FEATURE:
<223> OTHER INFORMATION: Artificially generated sequence for Bone
      Morphogenic Protein 2 73-92

<400> SEQUENCE: 4

Lys Ile Pro Lys Ala Ser Ser Val Pro Thr Glu Leu Ser Ala Ile Ser
1               5                   10                  15

Thr Leu Tyr Leu
            20

<210> SEQ ID NO 5
<211> LENGTH: 20
<212> TYPE: PRT
<213> ORGANISM: Artificial
<220> FEATURE:
<223> OTHER INFORMATION: Artificially generated sequence for Bone
      Morphogenic Protein-7 89-117

<400> SEQUENCE: 5

Thr Val Pro Lys Pro Ser Ser Ala Pro Thr Gln Leu Asn Ala Ile Ser
1               5                   10                  15

Thr Leu Tyr Phe
            20

<210> SEQ ID NO 6
<211> LENGTH: 20
<212> TYPE: PRT
<213> ORGANISM: Artificial
<220> FEATURE:
<223> OTHER INFORMATION: Artificially generated sequence for Bone
      Morphogenic Protein-9 68-87
<220> FEATURE:
<221> NAME/KEY: misc_feature
<223> OTHER INFORMATION: BMP-9 68-87

<400> SEQUENCE: 6

Lys Val Gly Lys Ala Ser Ser Val Pro Thr Lys Leu Ser Pro Ile Ser
1               5                   10                  15

Ile Leu Tyr Lys
            20

<210> SEQ ID NO 7
<211> LENGTH: 18
<212> TYPE: DNA
<213> ORGANISM: Artificial
<220> FEATURE:
<223> OTHER INFORMATION: Artificially generated forward primer sequence
      for hGAPDH
<220> FEATURE:
<221> NAME/KEY: misc_feature
<223> OTHER INFORMATION: hGAPDH primer (forward sequence)
```

<400> SEQUENCE: 7
gacagtcagc cgcatctt                                        18

<210> SEQ ID NO 8
<211> LENGTH: 20
<212> TYPE: DNA
<213> ORGANISM: Artificial
<220> FEATURE:
<223> OTHER INFORMATION: Artificially generated reverse primer sequence
      for hGAPDH
<220> FEATURE:
<221> NAME/KEY: misc_feature
<223> OTHER INFORMATION: hGAPDH primer (reverse sequence)

<400> SEQUENCE: 8
ccatggtgtc tgagcgatgt                                      20

<210> SEQ ID NO 9
<211> LENGTH: 20
<212> TYPE: DNA
<213> ORGANISM: Artificial
<220> FEATURE:
<223> OTHER INFORMATION: Artificially generated forward primer sequence
      for hRunx2
<220> FEATURE:
<221> NAME/KEY: misc_feature
<223> OTHER INFORMATION: hRunx2 primer (forward sequence)

<400> SEQUENCE: 9
ggacgaggca agagtttcac                                      20

<210> SEQ ID NO 10
<211> LENGTH: 26
<212> TYPE: DNA
<213> ORGANISM: Artificial
<220> FEATURE:
<223> OTHER INFORMATION: Artificially generated reverse primer sequence
      for hRunx2
<220> FEATURE:
<221> NAME/KEY: misc_feature
<223> OTHER INFORMATION: hRunx2 primer (reverse sequence)

<400> SEQUENCE: 10
artcacaagc ttctgtctgt gccttc                               26

<210> SEQ ID NO 11
<211> LENGTH: 20
<212> TYPE: DNA
<213> ORGANISM: Artificial
<220> FEATURE:
<223> OTHER INFORMATION: Artificially generated forward primer sequence
      for hBSP
<220> FEATURE:
<221> NAME/KEY: misc_feature
<223> OTHER INFORMATION: hBSP primer (forward sequence)

<400> SEQUENCE: 11
cctggcacag ggtatacagg                                      20

<210> SEQ ID NO 12
<211> LENGTH: 20
<212> TYPE: DNA
<213> ORGANISM: Artificial
<220> FEATURE:
<223> OTHER INFORMATION: Artificially generated reverse primer sequence
      for hBSP
<220> FEATURE:
<221> NAME/KEY: misc_feature
<223> OTHER INFORMATION: hBSP primer (reverse sequence)

```
<400> SEQUENCE: 12
ctgcttcgct ttcttcgttt                                           20

<210> SEQ ID NO 13
<211> LENGTH: 15
<212> TYPE: DNA
<213> ORGANISM: Artificial
<220> FEATURE:
<223> OTHER INFORMATION: Artificially generated forward primer sequence
      for hOCN
<220> FEATURE:
<221> NAME/KEY: misc_feature
<223> OTHER INFORMATION: hOCN primer (forward sequence)

<400> SEQUENCE: 13
catgagagcc ctcac                                                15

<210> SEQ ID NO 14
<211> LENGTH: 17
<212> TYPE: DNA
<213> ORGANISM: Artificial
<220> FEATURE:
<223> OTHER INFORMATION: Artificially generated reverse primer sequence
      for hOCN
<220> FEATURE:
<221> NAME/KEY: misc_feature
<223> OTHER INFORMATION: hOCN primer (reverse sequence)

<400> SEQUENCE: 14
agagcgacac cctagac                                              17

<210> SEQ ID NO 15
<211> LENGTH: 23
<212> TYPE: DNA
<213> ORGANISM: Artificial
<220> FEATURE:
<223> OTHER INFORMATION: Artificially generated forward primer sequence
      for hCD31
<220> FEATURE:
<221> NAME/KEY: misc_feature
<223> OTHER INFORMATION: hCD31 primer (forward sequence)

<400> SEQUENCE: 15
tctatgacct cgccctccac aaa                                       23

<210> SEQ ID NO 16
<211> LENGTH: 27
<212> TYPE: DNA
<213> ORGANISM: Artificial
<220> FEATURE:
<223> OTHER INFORMATION: Artificially generated reverse primer sequence
      for hCD31
<220> FEATURE:
<221> NAME/KEY: misc_feature
<223> OTHER INFORMATION: hCD31 primer (reverse sequence)

<400> SEQUENCE: 16
gaacggtgtc ttcaggttgg tatttca                                   27
```